(12) United States Patent
Liu

(10) Patent No.: US 10,492,899 B2
(45) Date of Patent: Dec. 3, 2019

(54) FULL-FUNCTION ARTIFICIAL ORGAN FITTING BODY AS WELL AS PREPARATION AND CULTURE METHODS THEREOF

(71) Applicant: Chang Liu, Beijing (CN)

(72) Inventor: Chang Liu, Beijing (CN)

( * ) Notice: Subject to any disclaimer, the term of this patent is extended or adjusted under 35 U.S.C. 154(b) by 0 days.

(21) Appl. No.: 15/694,943

(22) Filed: Sep. 4, 2017

(65) Prior Publication Data

US 2017/0360551 A1 Dec. 21, 2017

Related U.S. Application Data

(63) Continuation of application No. PCT/CN2015/079793, filed on May 26, 2015.

(30) Foreign Application Priority Data

Mar. 4, 2015 (CN) .......................... 2015 1 0096765

(51) Int. Cl.
*A61F 2/04* (2013.01)
*A61F 2/06* (2013.01)
(Continued)

(52) U.S. Cl.
CPC .............. *A61F 2/04* (2013.01); *A61F 2/0077* (2013.01); *A61F 2/02* (2013.01); *A61F 2/06* (2013.01); *A61L 27/26* (2013.01); *A61L 27/383* (2013.01); *A61L 27/3808* (2013.01); *A61L 27/3886* (2013.01); *A61L 27/3895* (2013.01); *A61L 27/52* (2013.01); *A61L 27/54* (2013.01); *C12M 21/08* (2013.01); *C12M 23/14* (2013.01); *C12M 25/14* (2013.01); *C12M 29/00* (2013.01); *C12M 41/34* (2013.01); *C12N 5/0062* (2013.01); *C12N 5/069* (2013.01); *C12N 5/0618* (2013.01);
(Continued)

(58) Field of Classification Search
CPC .......... A61F 2/022; A61F 2/0077; A61F 2/04; A61F 2240/001; A61L 27/52; A61L 2430/20; A61L 2430/22; B33Y 80/00
See application file for complete search history.

(56) References Cited

U.S. PATENT DOCUMENTS

| 4,391,909 A | 7/1983 | Lim |
| 6,227,202 B1 * | 5/2001 | Matapurkar ............... A61F 2/04 623/11.11 |
| 9,050,180 B1 * | 6/2015 | Kong ...................... A61L 27/52 |

FOREIGN PATENT DOCUMENTS

| CN | 1806774 A | 7/2006 |
| CN | 102871771 A | 1/2013 |
| CN | 103767804 A | 5/2014 |

OTHER PUBLICATIONS

Yoo et al., Bioprinting technology and its applications, European Journal of Cardio-Thoracic Surgery 46 (2014) 342-348 (Year: 2014).*

* cited by examiner

*Primary Examiner* — Brian E Pellegrino
(74) *Attorney, Agent, or Firm* — Erson IP (Nelson IP)

(57) ABSTRACT

A full-function artificial organ fitting body comprises a cortex layer and an organ body tissue area. The organ body tissue area comprises a growth area, a differentiation area, a docking area, a branch arterial system, a branch nervous system and a branch venous system. The branch arterial system, the branch nervous system and the branch venous system are distributed in the differentiation area and form a main body three-dimensional skeleton structure with the outer growth area and the middle docking area.

1 Claim, 2 Drawing Sheets

(51) Int. Cl.
  *A61L 27/38* (2006.01)
  *A61F 2/02* (2006.01)
  *A61F 2/00* (2006.01)
  *A61L 27/26* (2006.01)
  *A61L 27/52* (2006.01)
  *A61L 27/54* (2006.01)
  *C12M 3/00* (2006.01)
  *C12M 1/00* (2006.01)
  *C12M 1/12* (2006.01)
  *C12M 1/34* (2006.01)
  *C12N 5/00* (2006.01)
  *C12N 5/079* (2010.01)
  *C12N 5/071* (2010.01)

(52) U.S. Cl.
  CPC ....... *A61F 2/022* (2013.01); *A61F 2002/0086* (2013.01); *A61F 2240/001* (2013.01); *A61L 2300/414* (2013.01); *C12N 2513/00* (2013.01); *C12N 2537/10* (2013.01)

FULL-FUNCTION ARTIFICIAL ORGAN FITTING BODY AS WELL AS PREPARATION AND CULTURE METHODS THEREOF

CROSS-REFERENCE TO RELATED APPLICATIONS

This application is a continuation of International Patent Application No. PCT/CN2015/079793 with a filing date of May 26, 2015, designating the United States, and further claims priority to Chinese Patent Application No. 201510096765.4 with a filing date of Mar. 4, 2015. The content of the aforementioned applications, including any intervening amendments thereto, are incorporated herein by reference.

FIELD OF THE INVENTION

The present invention relates to a full-function artificial organ fitting body as well as preparation and culture methods thereof, and belongs to interdisciplinary fields of biology, materials, machinery and manufacture.

BACKGROUND OF THE INVENTION

More than ten millions of patients suffer from tissue defects or organ failure every year in the world, and about 8 million of the patients are treated by surgical operations each year in America only. However, living donor tissue organs are limited, and an existing mechanical apparatus does not have all functions of complicated tissue organs and cannot prevent further deterioration of diseases of the patients. In recent ten years, scientists perform in-vitro reproduction by utilizing a small amount of normal cells of residual human organs by using a tissue engineering technology, and obtain organs with the same function needed by the patients. The organs do not have a rejection reaction, and favorable results are achieved. Many newly established biotechnology companies are getting ready to invest large sums of money for realizing commercialization. An industry with a value of 4 billion dollars is formed and progressively increased at a speed of 25% per year in America. However, an existing tissue engineering technology faces many difficulties and limitations, and successes achieved by tissue engineering application research exist in tissues with relatively simple structures and physiological functions, such as skeleton and cartilage. A traditional scaffold preparation technology cannot accurately sizes, structures, space distribution and penetrating channels of pores, and nutrition supply and vascular growth are greatly limited. A structural scaffold is first prepared in a traditional tissue engineering method generally; and since most of oxygen and nutrition are consumed by upper cells in a cell culture process, these components are prevented from diffusing to a bottom layer, thereby limiting migration of the cells to a deep layer of the scaffold. Such a method for sequentially preparing the scaffold and then culturing the cells consumes time and labor, and the cells may be varied and aged in a process of migrating into the scaffold, so that a requirement of treating clinical patients in time cannot be met. Meanwhile, the traditional tissue engineering technology cannot meet needs for accurately and spatially positioning and placing different cells at fixed points and constructing functional gradient structures of the complicated tissue organs.

3D printing (three-dimensional printing, 3DP) is also called rapid prototyping (RP) or additive manufacturing (AM), thereby realizing formation of a structural body by utilizing layer-by-layer stacking of materials. Many foreign scientific research teams realize assembling or printing of a cell-containing three-dimensional structural body based on an RP technology, such as a three-dimensional fibrous deposition technology in a medical center of Utrecht University [Fedorovich N E, et al. Tissue Engineering Part C, 2011, 18(1):33], a three-dimensional direct writing bioprinting technology of University of Arizona [Cooper G M, et al. Tissue Engineering Part A, 2010, 16(5):1749], etc. A Center of Organ Manufacturing in Tsinghua University in China develops a melted extrusion modeling device and a single (double)-end nozzle (needle) low-temperature deposition forming device and successfully prepares simple vascular nets, hepatic tissues, bone repair materials and the like [Wang X H, et al. Trends in Biotechnology, 2007, 25:505; Wang X H, et al. Tissue Engineering Part B, 2010, 16:189; Wang X H. Artificial organs, 2012, 36:591].

The 3DP has many manners. For example, a porous hollow structure is prepared by utilizing the RP technology in University of Science and Technology of China and Dalian University of Technology. The porous hollow structure saves raw materials and can guarantee original characters and mechanical properties [Wang W, et al. ACM Transactions on Graphics (TOG), 2013, 32(6):177]. Vozzi G, et al. in University of Pisa prepare a hexagonal mesh by utilizing a microinjection method, and a forming structure is accurate [Vozzi G, et al. Tissue Engineering, 2002, 8(6):1089-1098]. A preparation method for preparing the above hollow structure is limited to a field of synthetic polymeric materials. An application of the preparation method in a biological and hydrogel system is seldom mentioned. An application of a hollow hydrogel structure contributes to increasing an exchange speed of a nutrient solution in the structural body.

A microfluidics technology (MT) can control, operate and detect complicated fluid under a microscopic size and emerges rapidly in fields of micromechanics, bioengineering and the like in recent years, and then a lab on a chip appears at the right moment. Capel A J, et al. in Loughborough University summarize applications of five rapid prototyping technologies in a fluid chemical reaction and propose a preparation method for preparing a small-sized reactor [Capel A J, et al. Lab on a Chip, 2013, 13(23):4583]. A combination of the 3D printing technology and the microfluidics technology is a research hotspot for solving artificial organ manufacturing. For example, Miller J S, et al. in University of Pennsylvania prepare a three-dimensional soluble sugar fiber scaffold, and the sugar fiber scaffold is introduced into blood to simulate an effect of a shear force, thereby completing adhesion of endothelial cells in a vessel channel and realizing a primary vascular function [Miller J S, et al. Nature materials, 2012, 11(9):768]. However, preparation of the sugar fiber scaffold consumes time and labor, and precision and geometry complexity are also limited.

A patent literature (with an application number of 201210324600.4) proposes a method for preparing a spindle-shaped complex organ precursor by using a rotary composite mold. According to the method, an arc at a periphery of a formed body is obtained through relative rotation of the mold, and a semi-spindle-shaped formed body with branch channels is obtained through a pouring method. However, in the method, controllability of fine structures of the branch channels is low, multiple branches of the branch channels are difficult to be guaranteed, and operating stability, structural complexity and the like remain to be improved.

A patent literature (with an application number of 201410026170.7) proposes a rapid prototyping method for preparing a vascularized tissue structure with a microfluidic channel. The structure prepared by the method only contains a one-in one-out branch vessel system, cannot satisfy a need that a complex organ simultaneously contains branch artery and vein vascular systems and a nervous system, and cannot ensure that the constructed vascularized tissue structure has strong growth ability and metabolic functions after transplanted in vivo.

Through the above analysis, construction of a full-function artificial organ by utilizing a regenerative medicine principle has become a research hotspot in medicine and engineering fields. The existing 3DP (AM), microfluidics technology and a combined mold technology cannot prepare a full-function implantable organ structure capable of simultaneously containing the branch artery and vein vascular system, the nervous system and an immune system and capable of being directly connected with human artery and vein vessels, nerves and other systems. These factors promote an organic combination of various different technologies, and full-function artificial organs with various system structures are prepared by utilizing a composite multi-nozzle 3D printing technology, in-mold pouring, spraying, electrospining and other technologies, thereby realizing composite forming of various biological materials including high polymer solutions, cell-containing hydrogel and cell-containing dilute solutions. The various systems distributed in the organs may be mutually promoted and synergetically developed. The present invention establishes a theoretical and practical foundation for manufacturing the full-function artificial organs.

SUMMARY OF THE INVENTION

A purpose of the present invention is to disclose a full-function artificial organ fitting body as well as preparation and culture methods thereof, so as to simulate natural animal organs in functions and structures, thereby realizing rapid manufacture of a plurality of complex tissue organs. The present invention is used for direct repair and replacement of failure organs, thereby achieving purposes of repair and regeneration and providing a new possibility for fields of organ manufacture, transplantation and the like.

Technical solutions of the present invention are as follows:

The full-function artificial organ fitting body comprises a cortex layer and an organ body tissue area, wherein the organ body tissue area comprises a growth area, a differentiation area, a docking area, a branch arterial system, a branch nervous system and a branch venous system; a structural shape of the cortex layer simulates an appearance of each organ of an animal; the branch arterial system, the branch nervous system and the branch venous system are distributed in the differentiation area and form a main body three-dimensional skeleton structure with the outer growth area and the middle docking area; the branch arterial system comprises a main artery and arterial branches; the branch venous system comprises a main vein and venous branches; the arterial branches and the venous branches are respectively connected with the middle docking area; the branch nervous system comprises a main nerve tract and nerve tract branches; the differentiation area is composed of natural polymeric hydrogel containing adult cells, or natural polymeric hydrogel containing growth factors and stem cells; the growth area is composed of natural polymeric hydrogel containing stem cells; the docking area is composed of natural polymeric hydrogel containing endothelial cells, or natural polymeric hydrogel containing the growth factors and the stem cells; the branch nervous system penetrates through the docking area and is continuously penetrated; the branch arterial system comprises at least one fluid inlet, at least contains one fluid outlet or does not have any outlet; the branch venous system comprises at least one fluid inlet and at least one fluid outlet; the cortex layer is a synthetic polymeric material and is divided into an upper part and a lower part; and the branch arterial system, the branch nervous system and the branch venous system are composed of the cell-containing natural polymeric hydrogel through layered perfusion by using a 3D printing layer-by-layer stacking or in-mold pouring technology.

The branch arterial system and the branch venous system in the present invention comprise at least one endovascular cortex layer composed of endothelial cells; the branch nervous system comprises a fiber bundle containing at least one kind of nerve cells; inner diameters of the arterial branches and the venous branches are 0.01-5 mm, and diameters of the nerve tract branches are 0.01-5 mm; and a layer thickness of the cell-containing hydrogel in the growth area, the differentiation area and the docking area is 0.01-20 mm.

An outer shape of the organ fitting body in the present invention is similar to the heart, kidney, liver, pancreas, breast, lung, skin, ears, uterus, brain or bladder of an animal.

The natural polymeric hydrogel in the differentiation area, the growth area and the docking area in the present invention is at least one of sodium alga acid with a mass percentage of 0.1-20%, collagen, dextrose, fibrinogen, bioactive peptide, gelatin, chitosan, an extracellular matrix, gelose, laminin, chondroitin sulfate, carrageenan, protein polysaccharide and a hyaluronic acid solution; one or more of inorganic salt with a mass percentage of 0.01-10%, an anticoagulation factor and a cryopreservation factor are compounded in the natural polymeric hydrogel; the cortex layer is at least one of synthetic polymeric polyurethane, polyethylene, polypropylene, polyvinyl chloride, polycaprolactone, polycarbonate, polyethylene glycol, poly(lactic-co-glycolic acid), polyester and polyglycolic acid ester; and a solvent of the synthetic polymeric solution is tetraethylene glycol or 1,4-dioxane, and a mass-volume percentage of the synthetic polymeric solution is 0.1-30%.

The adult cells in the present invention are at least one of cardiac muscle cells, hepatic cells, islet cells, stellate cells, osteoblast, cartilage cells, smooth muscle cells, fibroblast, endothelial cells, nephrocyte, Schwann's cells, neuroglial cells, epithelial cells, adipose cells, spleen cells, uterus cells and adipose cells; and the stem cells are at least one of mesenchymal stem cells, umbilical cord blood stem cells, bone marrow stem cells, embryonic stem cells and induced pluripotent stem cells.

A preparation method of the full-function artificial organ fitting body provided by the present invention comprises the following steps:

1) designing a shape structure, a branch arterial system structure, a branch venous system structure, a branch nervous system structure and a cortex layer structure of the full-function artificial organ respectively by adopting a three-dimensional computer modeling method;

2) preparing overall cortex layer molds with open upper ends and different diameters, and a three-dimensional skeleton structure of the branch arterial systems, the branch venous systems and the branch nervous systems by adopting the 3D printing or in-mold pouring technology; and respectively preparing a natural polymer aqueous solution containing the adult cells or containing a mixture of the growth factors and the stem cells, a natural polymer aqueous solution containing the stem cells and a natural polymer aqueous solution containing the endothelial cells, wherein a mass percentage of the natural polymer aqueous solution is 0.1-20%, and a density of the cells in the natural polymer aqueous solution is $1*10^{2-7}$ cells per mL;

3) putting the three-dimensional skeleton structure of at least one group of the branch arterial systems, one group of the branch venous systems and the branch nervous system into the overall cortex layer mold with a smallest diameter, pouring the natural polymer aqueous solution containing the adult cells or containing the mixture of the growth factors and the stem cells among the branch arterial systems, the branch venous systems, the branch nervous systems and the overall cortex layer mold to form a lower part of a differentiation area, and spraying or injecting the natural polymer solution containing the endothelial cells or a mixture of the stem cells and the growth factors on the structure to form the docking area;

4) placing a group of branch venous systems and branch nervous systems on an upper part of the docking area, or placing the branch arterial systems, the branch venous systems and the branch nervous systems, forming an upper part of a differentiation area from an opening at an upper end of the overall cortex layer mold according to a method in the step 3), and removing the overall cortex layer mold with the smallest diameter;

5) sleeving a second overall cortex layer mold with a larger diameter on an outer part of the prepared differentiation area, pouring the natural polymer solution containing the stem cells into a gap, and crosslinking or polymerizing natural polymers to form a main body three-dimensional skeleton structure containing the differentiation area and the growth area; and 6) removing the second overall cortex layer mold, coating a synthetic polymer solution layer outside the main body three-dimensional skeleton structure containing the differentiation area and the growth area, and extracting with an organic solvent to form the full-function organ fitting body containing a cortex layer structure.

Another preparation method of the full-function artificial organ fitting body provided by the present invention comprises the following steps:

1) designing a shape structure, a branch arterial system structure, a branch venous system structure, a branch nervous system structure and a cortex layer structure of the full-function artificial organ respectively by adopting a three-dimensional computer modeling method;

2) preparing cortex layer molds with different diameters, and a three-dimensional skeleton structure of the branch arterial systems, the branch venous systems and the branch nervous systems by adopting the 3D printing or in-mold pouring technology, wherein the cortex layer molds with different diameters are divided into an upper part and a lower part; and respectively preparing a natural polymer aqueous solution containing the adult cells or containing a mixture of the growth factors and the stem cells, a natural polymer aqueous solution containing the stem cells and a natural polymer aqueous solution containing the endothelial cells, wherein a mass percentage of the natural polymer aqueous solution is 0.1-20%, and a density of the cells in the natural polymer aqueous solution is $1*10^{2-7}$ cells per mL;

3) putting the three-dimensional skeleton structure of at least one group of the branch arterial systems, one group of the branch venous systems and the branch nervous system into a lower half part of the cortex layer mold with a smallest diameter, pouring the natural polymer aqueous solution containing the adult cells or containing the mixture of the growth factors and the stem cells among the branch arterial systems, the branch venous systems, the branch nervous systems and the lower half part of the cortex layer mold to form a lower part of a differentiation area, and spraying or injecting the natural polymer solution containing the endothelial cells or a mixture of the stem cells and the growth factors on the structure to form the docking area;

4) putting another group of branch arterial systems, the branch venous systems, the branch nervous systems and an upper half part of the cortex layer mold with the smallest diameter on the docking area, and forming the lower part of the differentiation area according to a method in the step 3);

5) sequentially sleeving the lower half part and the upper half part of the second cortex layer mold with a larger diameter on an outer part of an upper half part and a lower half part of the prepared differentiation area, pouring the natural polymer solution containing the stem cells into a gap, crosslinking or polymerizing natural polymers, and removing the second cortex layer mold to form a main body three-dimensional skeleton structure containing the differentiation area and the growth area; and 6) coating a synthetic polymer solution layer outside the main body three-dimensional skeleton structure containing the differentiation area and the growth area, and extracting with an organic solvent to form the full-function organ fitting body containing a cortex layer structure.

A culture apparatus of the full-function artificial organ fitting body provided by the present invention comprises at least one inner airbag, an outer airbag, an inner airbag gas delivery apparatus, an outer airbag gas delivery apparatus, a sealing structure, an organ fitting body, a culture bottle, a fluid delivery apparatus and an airbag controller, wherein the inner airbag gas delivery apparatus and the outer airbag gas delivery apparatus are respectively connected with the inner airbags and the outer airbag through gas pipelines; the inner airbags are put into the organ fitting body; the organ fitting body is put into the outer airbag; the culture bottle is filled with a culture solution; the culture solution is communicated with the organ fitting body through a fluid pipeline; the sealing structure is arranged at inlets of the inner airbags and the outer airbag; and the airbag controller is respectively connected with the inner airbag gas delivery apparatus and the outer airbag gas delivery apparatus through a control circuit.

According to the culture apparatus in the present invention, the fluid delivery apparatus adopts a fluid pump, a siphon and a hydrophilic sponge drainage tube.

A culture method of the full-function artificial organ fitting body provided by the present invention comprises the following steps:

1) manufacturing inner airbags and an outer airbag, enabling shapes of the inner airbags to be consistent with shapes of an arterial system and a venous system in the full-function artificial organ fitting body, and disinfecting for later use;

2) respectively putting the inner airbags into the branch arterial systems and the branch venous systems, putting the full-function artificial organ fitting body with the inner airbags into the outer airbag together, connecting a branch artery inner airbag and a branch vein inner airbag with the inner airbag gas delivery apparatus through the gas pipelines, and connecting the outer airbag with the outer airbag gas delivery apparatus through the gas pipelines;

3) injecting gases into the inner airbags and the outer airbag to inflate the airbags, and sealing openings of the inner airbags and the outer airbag through the sealing structure; adding a cell culture solution into the culture bottle, and delivering the cell culture solution into the full-function artificial organ fitting body through the fluid delivery apparatus;

4) controlling inflation and deflation amplitudes and rhythm ranges of the inner airbags and the outer airbag through the airbag controller, so that in inflation and deflation processes of the inner airbags and the outer airbag, on one hand, the culture solution flows or permeates through a microporous structure of the hydrogel in the organ fitting body, and needs of growth proliferation and metabolism of cells in each area are met, and on the other hand, the organ fitting body is stressed by a three-dimensional tension-compression stress, connection is established among the cells, and orientated growth and arrangement of the cells may be realized; and 5) controlling the inflation and deflation amplitudes of the inner airbags and the outer airbag to be 0.01-10 mm, and controlling the rhythm ranges of the inner airbags and the outer airbag to be 20-200 times per minute, wherein the inner airbags and the outer airbag can radially drive the organ fitting body to inflate and deflate along a same axis, or can stretch or extrude the organ fitting body in opposite directions.

Compared with the prior art, the present invention has advantages and outstanding effects as follows: the present invention can realize accurate positioning of different cells and matrix materials in space by utilizing computer modeling and cell assembling technologies, and overcome defects in current tissue engineering that cell induction and culture in a three-dimensional scaffold need a long time, distribution of the cells in the scaffold is non-uniform, the cells are difficult to penetrate into a deeper structure, and the like. Structures and functions of various organs in a human body are simulated in the present invention, thereby realizing construction of the full-function artificial organ fitting body on a three-dimensional scale. Moreover, through controllable three-dimensional stress field training or culturing, cells in each organ fitting body are arranged in a certain direction to form different tissue areas, thereby increasing mechanical strength of the full-function artificial organs and enabling the organs to have some special functions. Meanwhile, the needs of growth proliferation and metabolism of the cells are met, thereby completing a change from the artificial organ fitting body to a natural organ direction. In addition, the present invention can further simulate the branch arterial systems, the branch venous systems and the branch nervous systems in various organs, and realize functions of anticoagulant functions, anti-suture functions and heart pumping functions of blood vascular systems, thereby achieving purposes of repair and regeneration of various failure organs.

BRIEF DESCRIPTION OF THE DRAWINGS

in FIG. 1, 101—cortex layer; 102—organ body tissue area; 103—growth area; 104—differentiation area; 105—docking area; 106—branch arterial system; 107—branch nervous system; and 108—branch venous system.

In FIG. 2, 1—airbag controller; 2—inner airbag gas delivery apparatus; 3—outer airbag gas delivery apparatus; 4—outer airbag; 5—first inner airbag; 6—sealing structure; 7—second inner airbag; 8—organ fitting body; 9—culture bottle; and 10—fluid delivery apparatus.

DETAILED DESCRIPTION OF THE EMBODIMENTS

The present invention is further described below in combination with drawings and embodiments.

Figure 1:
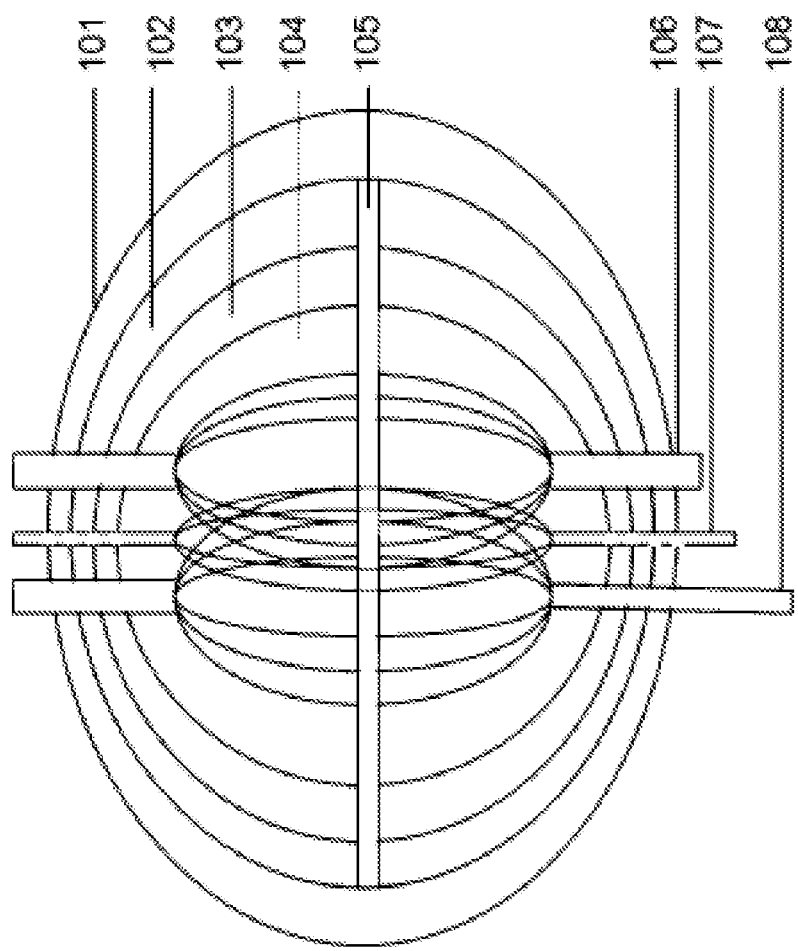
FIG. 1 is a schematic diagram of a three-dimensional structure of a full-function artificial organ fitting body.

As shown in FIG. 1, a full-function artificial organ fitting body provided by the present invention comprises a cortex layer 101 and an organ body tissue area 102, wherein the organ body tissue area comprises a growth area 103, a differentiation area 104, a docking area 105, a branch arterial system 106, a branch nervous system 107 and a branch venous system 108; a structural shape of the cortex layer 101 simulates an appearance of each organ of an animal; the branch arterial system 106, the branch nervous system 107 and the branch venous system 108 are distributed in the differentiation area 104 and form a main body three-dimensional skeleton structure with the outer growth area 103 and the middle docking area 105; the branch arterial system 106 comprises a main artery and arterial branches; the branch venous system 108 comprises a main vein and venous branches; the arterial branches and the venous branches are respectively connected with the middle docking area 105; the branch nervous system 108 comprises a main nerve tract and nerve tract branches; the differentiation area 104 is composed of natural polymeric hydrogel containing adult cells, or natural polymeric hydrogel containing growth factors and stem cells; adult cells are at least one of cardiac muscle cells, hepatic cells, islet cells, stellate cells, osteoblast, cartilage cells, smooth muscle cells, fibroblast, endothelial cells, nephrocyte, Schwann's cells, neuroglial cells, epithelial cells, adipose cells, spleen cells, uterus cells and adipose cells; and the stem cells are at least one of mesenchymal stem cells, umbilical cord blood stem cells, bone marrow stem cells, embryonic stem cells and induced pluripotent stem cells.

The growth area 103 is composed of natural polymeric hydrogel containing stem cells; the docking area 105 is composed of natural polymeric hydrogel containing endothelial cells, or natural polymeric hydrogel containing the growth factors and the stem cells; the branch nervous system 108 penetrates through the docking area 105 and is continuously penetrated; the branch arterial system 106 comprises at least one fluid inlet, at least contains one fluid outlet or does not have any outlet; the branch venous system 108 comprises at least one fluid inlet and at least one fluid outlet; the cortex layer 101 is a synthetic polymeric material and is divided into an upper part and a lower part; the branch arterial system 106, the branch nervous system 107 and the branch venous system 108 are composed of the cell-containing natural polymeric hydrogel through layered perfusion by using the 3D printing layer-by-layer stacking or in-mold pouring technology; and an outer shape of the organ fitting body is similar to the heart, kidney, liver, pancreas, breast, lung, skin, ears, uterus, brain or bladder and the like of an animal.

The branch arterial system and the branch venous system comprise at least one endovascular cortex layer composed of the endothelial cells; the branch nervous system comprises a fiber bundle composed of at least one kind of nerve cells; inner diameters of the arterial branches and the venous branches are 0.01-5 mm, and diameters of the nerve tract branches are 0.01-5 mm; and a layer thickness of the cell-containing hydrogel in the growth area, the differentiation area and the docking area is 0.01-20 mm.

The natural polymeric hydrogel in the differentiation area, the growth area, and the docking area is at least one of sodium alga acid with a mass percentage of 0.1-20%, collagen, dextrose, fibrinogen, a bioactive peptide, gelatin, chitosan, an extracellular matrix, gelose, laminin, chondroitin sulfate, carrageenan, protein polysaccharide and a hyaluronic acid solution; one or more of an inorganic salt with a mass percentage of 0.01-10%, an anticoagulation factor and a cryopreservation factor are compounded in the natural polymeric hydrogel; the cortex layer is at least one of synthetic polymeric polyurethane, polyethylene, polypropylene, polyvinyl chloride, polycaprolactone, polycarbonate, polyethylene glycol, poly(lactic-co-glycolic acid), polyester and polyglycolic acid ester; and a solvent of the synthetic polymeric solution is tetraethylene glycol or 1,4-dioxane, and a mass-volume percentage of the synthetic polymeric solution is 0.1-30%.

Figure 2:
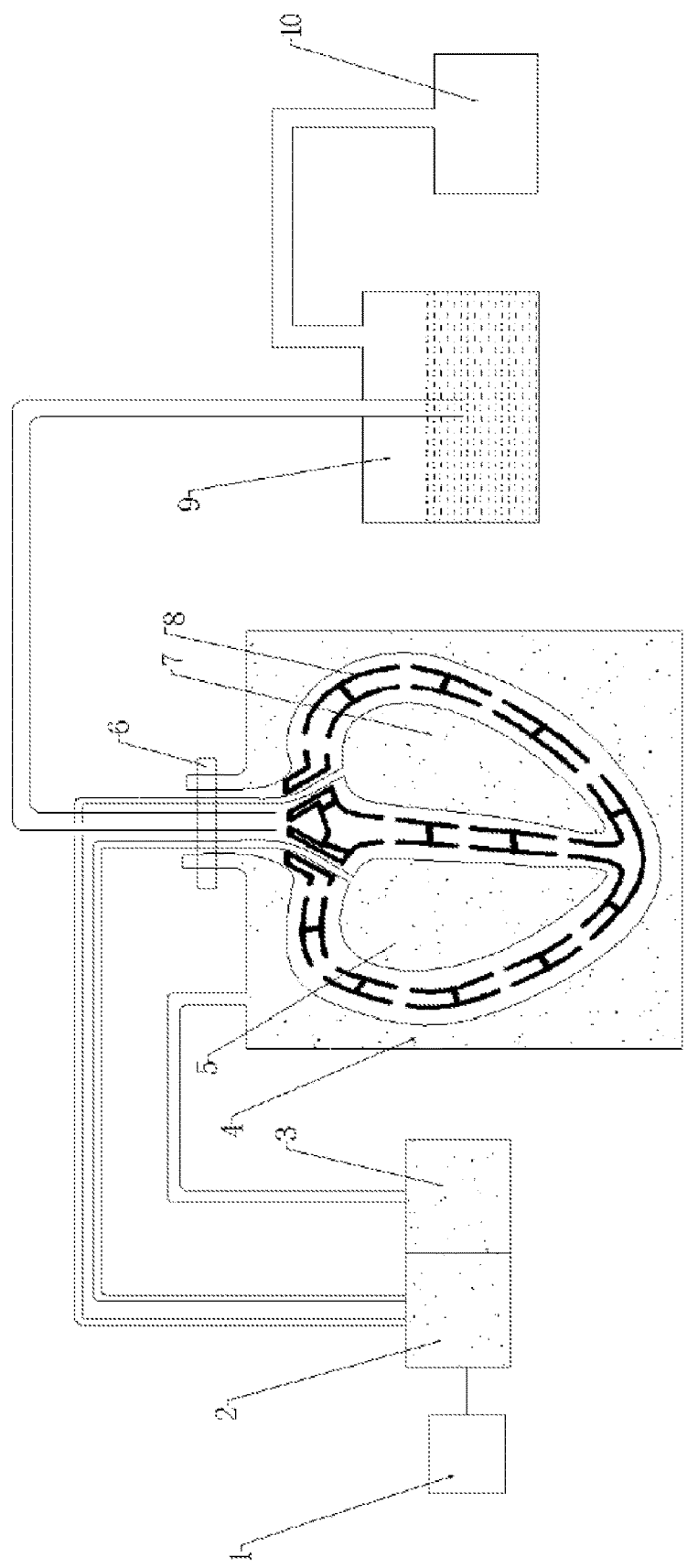
FIG. 2 is a schematic diagram of a structure principle of a culture apparatus of a full-function artificial organ fitting body.

A preparation method of the full-function artificial organ fitting body provided by the present invention comprises the following steps:

a) designing a shape structure, a branch arterial system structure, a branch venous system structure, a branch nervous system structure and a cortex layer structure of the full-function artificial organ respectively by adopting a three-dimensional computer modeling method, specifically as follows: a three-dimensional model of the shape structure, the cortex layer mold, the branch arterial system structure, the branch venous system structure and the branch nervous system structure of the full-function artificial organ fitting body is designed by using computer-aided design software (such as SolidWorks) according to structural and functional characteristics of human organs (such as the heart, the liver, the kidney, etc.). Characteristics of the model are as follows: for a symmetrical or asymmetrical three-dimensional structure encircled by a smooth curved surface, a cavity is composed of cell-containing hydrogel with a certain thickness, and the hydrogel contains a microporous structure, so that a culture solution (cultured in vitro) or blood (implanted in vivo) can circulate in the organ fitting body;

2) preparing an overall cortex layer mold with an open upper end or a cortex layer mold containing an upper part and a lower part, and a three-dimensional skeleton structure of a group of branch artery or branch venous systems and the branch nervous systems by adopting the 3D printing or in-mold pouring technology, specifically as follows: seed cells are purchased or extracted, and selected biological materials are dissolved in a solution to prepare the natural polymeric hydrogel; the natural polymeric hydrogel is at least one of sodium alga acid with a mass percentage of 0.1-20%, collagen, dextrose, fibrinogen, bioactive peptide, gelatin, chitosan, an extracellular matrix, gelose, laminin, chondroitin sulfate, carrageenan, protein polysaccharide and a hyaluronic acid solution; and one or more of inorganic salt with a mass percentage of 0.01-10%, an anticoagulation factor and a cryopreservation factor are compounded in the natural polymeric hydrogel;

3) combining the overall cortex layer mold with the open upper end or the lower part of the cortex layer mold, and a three-dimensional skeleton structure of at least one group of the branch arterial systems, one group of the branch venous systems and the branch nervous system together, and arranging the hydrogel containing the cells and growth factors in a position of the three-dimensional skeleton structure to form a partial main body three-dimensional skeleton structure by adopting micro-droplet jetting, perfusion, injection or pouring technologies; spraying or injecting a natural polymer dilute solution containing endothelial cells or stem cells/endothelial cell growth factors on the structure to form a docking area; combining the upper part of the overall cortex layer mold and a three-dimensional skeleton structure of a group of the branch arterial systems, at least one group of the branch venous systems and the branch nervous system together on the docking area, and arranging the hydrogel containing the cells and growth factors in a position of the three-dimensional skeleton structure to form a main body three-dimensional skeleton structure by adopting the micro-droplet jetting, perfusion, injection or pouring technologies;

4) removing the upper part and the lower part of the cortex layer mold, compounding some synthetic polymer solutions to an outer side of the main body three-dimensional skeleton structure by adopting adhesion, spraying or electrospining technologies, and extracting the polymer solution with phosphate buffer, a cell culture medium, normal saline, serum or body fluid to form a cortex structure; and 5) performing in-vitro culture on the full-function artificial organ fitting body by adopting a culture apparatus shown as FIG. 2 or a pulsatile bioreactor, compounding different growth factors into the cell culture solution (in a cocktail release manner) for realizing stepwise induction of the stem cells, wherein after a period of induction and training, on one hand, various layers of cells are tightly contacted under an effect of a three-dimensional normal stress, thereby establishing connection and forming tissues among the cells; and on the other hand, circulation of nutrient substances in the artificial organ fitting body is promoted, thereby meeting needs of growth proliferation and metabolism of cells and completing a change from the artificial organ fitting body to a special organ function.

The preparation method in the present invention specifically comprises two solutions as follows:

A first preparation method comprises specific steps:

1) designing the shape structure, the branch arterial system structure, the branch venous system structure, the branch nervous system structure and the cortex layer structure of the full-function artificial organ respectively by adopting a three-dimensional computer modeling method;

2) preparing overall cortex layer molds with open upper ends and different diameters, and the three-dimensional skeleton structure of the branch arterial systems, the branch venous systems and the branch nervous systems by adopting the 3D printing or in-mold pouring technology; and respectively preparing the natural polymer aqueous solution containing the adult cells or containing a mixture of the growth factors and the stem cells, a natural polymer aqueous solution containing the stem cells and a natural polymer aqueous solution containing the endothelial cells, wherein a mass percentage of the natural polymer aqueous solution is 0.1-20%, and a density of the cells in the natural polymer aqueous solution is $1*10^{2-7}$ cells per mL;

3) putting the three-dimensional skeleton structure of at least one group of the branch arterial systems, one group of the branch venous systems and the branch nervous system into the overall cortex layer mold with the smallest diameter, pouring the natural polymer aqueous solution containing the adult cells or containing the mixture of the growth factors and the stem cells among the branch arterial systems, the branch venous systems, the branch nervous systems and the overall cortex layer mold to form a lower part of the differentiation area, and spraying or injecting the natural polymer solution containing the endothelial cells or a mixture of the stem cells and the growth factors on the structure to form the docking area;

4) putting a group of branch venous systems and branch nervous systems on an upper part of the docking area, or putting the branch arterial systems, the branch venous systems and the branch nervous systems, forming an upper part of the differentiation area from an opening at an upper end of the overall cortex layer mold according to a method in the step 3), and removing the overall cortex layer mold with the smallest diameter;

5) sleeving a second overall cortex layer mold with a larger diameter on an outer part of the prepared differentiation area, pouring the natural polymer solution containing the stem cells into a gap, and crosslinking or polymerizing natural polymers to form a main body three-dimensional skeleton structure containing the differentiation area and the growth area; and 6) removing the second overall cortex layer mold, coating a synthetic polymer solution layer outside the main body three-dimensional skeleton structure containing the differentiation area and the growth area, and extracting with an organic solvent to form the full-function organ fitting body containing the cortex layer structure.

The other preparation method provided by the present invention comprises the following steps:

1) designing the shape structure, the branch arterial system structure, the branch venous system structure, the branch nervous system structure and the cortex layer structure of the full-function artificial organ respectively by adopting a three-dimensional computer modeling method;

2) preparing cortex layer molds with different diameters and the three-dimensional skeleton structure of the branch arterial systems, the branch venous systems and the branch nervous systems by adopting the 3D printing or in-mold pouring technology, wherein the cortex layer molds with different diameters are divided into an upper part and a lower part; and respectively preparing a natural polymer aqueous solution containing the adult cells or containing a mixture of the growth factors and the stem cells, a natural polymer aqueous solution containing the stem cells and a natural polymer aqueous solution containing the endothelial cells, wherein a mass percentage of the natural polymer aqueous solution is 0.1-20%, and a density of the cells in the natural polymer aqueous solution is $1*10^{2-7}$ cells per mL;

3) putting the three-dimensional skeleton structure of the at least one group of the branch arterial systems, the group of the branch venous systems and the branch nervous system into the lower half part of the cortex layer mold with a smallest diameter, pouring the natural polymer aqueous solution containing the adult cells or containing the mixture of the growth factors and the stem cells among the branch arterial systems, the branch venous systems, the branch nervous systems and the lower half part of the cortex layer mold to form a lower part of a differentiation area, and spraying or injecting the natural polymer solution containing the endothelial cells or a mixture of the stem cells and the growth factors on the structure to form the docking area;

4) putting another group of branch arterial systems, the branch venous systems, the branch nervous systems and an upper half part of the cortex layer mold with the smallest diameter on the docking area, and forming the lower part of the differentiation area according to the method in the step 3);

5) sequentially sleeving the lower half part and the upper half part of a second cortex layer mold with a larger diameter on an outer part of an upper half part and a lower half part of the prepared differentiation area, pouring the natural polymer solution containing the stem cells into a gap, crosslinking or polymerizing natural polymers, and removing the second cortex layer mold to form a main body three-dimensional skeleton structure containing the differentiation area and the growth area; and 6) coating a synthetic polymer solution layer outside the main body three-dimensional skeleton structure containing the differentiation area and the growth area, and extracting with an organic solvent to form the full-function organ fitting body containing the cortex layer structure.

FIG. 2 is a schematic diagram of a structure principle of a culture apparatus of a full-function artificial organ fitting body. The culture apparatus comprises at least one inner airbag, an outer airbag, an inner airbag gas delivery apparatus 2, an outer airbag gas delivery apparatus 3, a sealing structure 6, an organ fitting body 8, a culture bottle 9, a fluid delivery apparatus 10 and an airbag controller 1. The inner airbag gas delivery apparatus 2 and the outer airbag gas delivery apparatus 3 are respectively connected with the inner airbags and the outer airbag through gas pipelines; the inner airbags are put into the organ fitting body 8; the organ fitting body 8 is put into the outer airbag 4; the culture bottle 9 is filled with a culture solution; the culture solution is communicated with the organ fitting body through a fluid pipeline; the sealing structure 6 is formed at inlets of the inner airbags and the outer airbag 4; and the airbag controller 1 is respectively connected with the inner airbag gas delivery apparatus 2 and the outer airbag gas delivery apparatus 3 through a control circuit.

The full-function organ fitting body is cultured by utilizing the culture apparatus through specific steps as follows:

1) manufacturing the inner airbags and the outer airbag, enabling shapes of the inner airbags to be consistent with shapes of an arterial system and a venous system in the full-function artificial organ fitting body, and disinfecting for later use;

2) respectively putting the inner airbags into the branch arterial systems and the branch venous systems, putting the full-function artificial organ fitting body with the inner airbags into the outer airbag 4 together, connecting a branch artery inner airbag and a branch vein inner airbag 7 with the inner airbag gas delivery apparatus 2 through the gas pipelines, and connecting the outer airbag with the outer airbag gas delivery apparatus 3 through the gas pipelines;

3) injecting gases into the inner airbags and the outer airbag to inflate the airbags, and sealing openings of the inner airbags and the outer airbag through the sealing structure 6; adding a cell culture solution into the culture bottle, and delivering the cell culture solution into the full-function artificial organ fitting body through the fluid delivery apparatus 10;

4) controlling inflation and deflation amplitudes and rhythm ranges of the inner airbags and the outer airbag through the airbag controller 1, so that in inflation and deflation processes of the inner airbags and the outer airbag, on one hand, the culture solution flows or permeates through a microporous structure of the hydrogel in the organ fitting body, and needs of growth proliferation and metabolism of cells in each area are met; and on the other hand, the organ fitting body is stressed by a three-dimensional tension-compression stress, connection is established among the cells, and orientated growth and arrangement of the cells may be realized; and 5) controlling the inflation and deflation amplitudes of the inner airbags and the outer airbag to be 0.01-10 mm, and controlling the rhythm ranges of the inner airbags and the outer airbag to be 20-200 times per minute, wherein the inner airbags and the outer airbag can radially drive the organ fitting body to inflate and deflate along a same axis, or can stretch or extrude the organ fitting body in opposite directions.

A flow of the gas in the inner airbags and the outer airbag is controlled by the airbag controller 1, thereby controlling the inflation and deflation amplitudes and rhythm ranges of the inner airbags and the outer airbag. When the outer airbag inflates and the inner airbags deflate, the artificial organ fitting body is stressed by the three-dimensional normal stress and then is deflated towards an interior of the cavity, and meanwhile, the nutrient solution flows from an exterior of the cavity to the interior of the cavity via a plurality of pores and vessel channels. When the outer airbag deflates and the inner airbags inflate, the artificial organ fitting body is stressed by a three-dimensional tensile stress and inflated towards the exterior of the cavity, and meanwhile, the nutrient solution flows from the interior of the cavity to the exterior of the cavity via the plurality of pores and vessel channels. After a period of training, on one hand, the various layers of cells are tightly contacted under the effect of the three-dimensional normal stress, thereby establishing connection and forming tissues among the cells; and on the other hand, circulation of nutrient substances in the artificial organ fitting body is promoted, thereby meeting needs of the growth proliferation and metabolism of cells and completing the change from the artificial organ fitting body to the special organ function.

The present invention is further understood in embodiments illustrated as follows:

Embodiment 1: A Full-Function Artificial Heart Fitting Body as Well as Preparation and Culture Methods Thereof The preparation and culture methods comprise the following steps:

a) designing a shape structure, a branch arterial system structure, a branch venous system structure, a branch nervous system structure and a cortex layer structure of an artificial heart respectively by adopting a three-dimensional computer modeling method, wherein the shape of the artificial heart is a "coconut"-shaped three-dimensional structure which is encircled by a smooth curved surface and is large in top and small in bottom; two atria and two ventricles are put into the artificial heart; and each atrium and each ventricle respectively have a nutrition channel connected with the outside;

b) respectively preparing a fibrinogen solution with a mass percentage of 1%; respectively mixing adult cardiac muscle cells, adipose-derived stem cells and Schwann's cells with the solution, wherein a density of the mixed cardiac muscle cells is $10^2$ cells per mL, a density of the adipose-derived stem cells is $10^6$ cells per mL, and a density of the Schwann's cells is $10^3$ cells per mL; adding cell cryopreservation agent glycerin with a mass percentage of 3%, an endothelial cell growth factor with a mass percentage of 0.1% and an anticoagulant heparin with a mass percentage of 1%; loading the fibrinogen solution containing cells into an extrusion nozzle assembly of a composite multi-nozzle three-dimensional printing device; and preparing overall cortex layer molds with open upper ends and different diameters and a three-dimensional skeleton structure of the branch arterial systems, the branch venous systems and the branch nervous systems by adopting the in-mold pouring technology;

putting the three-dimensional skeleton structure of at least one group of the branch arterial systems, one group of the branch venous systems and the branch nervous system into the overall cortex layer mold with a smallest diameter, pouring a solution containing the cardiac muscle cells, the glycerin and the heparin among the branch arterial systems, the branch venous systems, the branch nervous systems and the overall cortex layer mold, polymerizing fibrinogen molecules by using thrombin with a mass percentage of 1% to form a lower part of a differentiation area, and spraying the fibrinogen solution containing the density of the adipose-derived stem cells on the structure to form the docking area;

d) putting a group of branch venous systems and branch nervous systems on an upper part of the docking area, or putting the branch arterial systems, the branch venous systems and the branch nervous systems, forming an upper part of a differentiation area from an opening at an upper end of the overall cortex layer mold according to a method in the step c), and removing the overall cortex layer mold with the smallest diameter;

e) sleeving a second overall cortex layer mold with a larger diameter on an outer part of the prepared differentiation area, pouring the fibrinogen solution containing the adipose-derived stem cells into a gap, polymerizing the fibrinogen molecules by using the thrombin with the mass percentage of 1%, and forming a main body three-dimensional skeleton structure containing the differentiation area and the growth area;

f) removing the second overall cortex layer mold, coating a synthetic polymer polyurethane solution layer with the mass-volume percentage of 10% outside the main body three-dimensional skeleton structure containing the differentiation area and the growth area, and extracting with an organic solvent to form the full-function organ fitting body containing the cortex layer structure;

g) manufacturing two inner airbags (i.e. a first inner airbag 5 and a second inner airbag 7) and an outer airbag 4, enabling shapes of the inner airbags to be consistent with shapes of an arterial system and a venous system in a full-function artificial heart fitting body, and disinfecting for later use;

h) respectively putting the inner airbags into the branch arterial systems and the branch venous systems, putting the full-function artificial heart fitting body with the inner airbags into the outer airbag together, connecting a branch artery inner airbag and a branch vein inner airbag with the inner airbag gas delivery apparatus through the gas pipelines, and connecting the outer airbag with the outer airbag gas delivery apparatus through the gas pipelines;

i) injecting gases into the inner airbags and the outer airbag 4 to inflate the airbags, and sealing openings of the inner airbags and the outer airbag through the sealing structure; adding a cell culture solution into the culture bottle, and delivering the cell culture solution into the artificial heart fitting body through the fluid delivery apparatus; and j) enabling the inner airbags and the outer airbag to stretch or extrude the artificial heart fitting body in a same direction along a same axial direction, controlling the inflation and deflation amplitudes to be 0.2 mm, controlling the rhythm to be 120 times per minute, and controlling inflation and deflation amplitudes and rhythm ranges of the inner airbags and the outer airbag through the airbag controller, so that in the inflation and deflation processes of the inner airbags and the outer airbag, on one hand, the culture solution flows or permeates through a microporous structure of the hydrogel in the organ fitting body, and needs of growth proliferation and metabolism of cells in each area are met; and on the other hand, the artificial heart fitting body is stressed by a three-dimensional tension-compression stress, connection is established among the cells, and orientated growth and arrangement of the cells may be realized.

Embodiment 2: A Full-Function Artificial Atrium Fitting Body as Well as Preparation and Culture Methods Thereof The preparation and culture methods comprise the following steps:

a) designing a shape structure, a branch arterial system structure, a branch venous system structure, a branch nervous system structure and a cortex layer structure of a full-function artificial atrium respectively by adopting a three-dimensional computer modeling method;

b) preparing cortex layer molds with different diameters and a three-dimensional skeleton structure of the branch arterial systems, the branch venous systems and the branch nervous systems by adopting the in-mold pouring technology, wherein the cortex layer molds with different diameters are divided into an upper part and a lower part; and respectively preparing 1% of fibrinogen mixture containing cardiac muscle cells, adipose-derived stem cells and Schwann's cells, wherein a density of the mixed cardiac muscle cells is $10^3$ cells per mL, a density of the adipose-derived stem cells is $10^5$ cells per mL, and a density of the Schwann's cells is $10^7$ cells per mL; adding cell cryopreservation agent glycerin with a mass percentage of 5%, an endothelial cell growth factor with a mass percentage of 0.2% and an anticoagulant heparin with a mass percentage of 1%;

c) putting the three-dimensional skeleton structure of at least one group of the branch arterial systems, one group of the branch venous systems and the branch nervous system into the lower half part of the cortex layer mold with the smallest diameter, pouring a fibrinogen mixture containing the cardiac muscle cells and the adipose-derived stem cells among the branch arterial systems, the branch venous systems, the branch nervous systems and the lower half part of the cortex layer mold, polymerizing fibrinogen molecules by using a thrombin with a mass percentage of 1% to form a lower part of a differentiation area, and spraying or injecting the fibrinogen mixture containing the adipose-derived stem cells and endothelial growth factors on the structure to form the docking area;

d) putting another group of branch arterial systems, the branch venous systems, the branch nervous systems and the upper half part of the cortex layer mold with the smallest diameter on the docking area, and forming a lower part of a differentiation area according to the method in the step c);

e) sequentially sleeving the lower half part and the upper half part of a second cortex layer mold with a larger diameter on an outer part of an upper half part and a lower half part of the prepared differentiation area, pouring the fibrinogen solution containing the adipose-derived stem cells into a gap, polymerizing fibrinogen molecules by using the thrombin with a mass percentage of 1%, removing the second cortex layer mold, and forming a main body three-dimensional skeleton structure containing the differentiation area and the growth area;

f) coating a synthetic polymer polyurethane layer with a mass-volume percentage of 1% outside the main body three-dimensional skeleton structure containing the differentiation area and the growth area, and extracting with an organic solvent to form the full-function artificial atrium containing the cortex layer structure;

g) manufacturing inner airbags and an outer airbag, enabling shapes of the inner airbags to be consistent with shapes of an arterial system and a venous system in the full-function artificial atrium fitting body, and disinfecting for later use;

h) respectively putting the inner airbags into the branch arterial systems and the branch venous systems, putting the full-function artificial atrium fitting body with the inner airbags into the outer airbag together, connecting a branch artery inner airbag and a branch vein inner airbag with the inner airbag gas delivery apparatus through the gas pipelines, and connecting the outer airbag with the outer airbag gas delivery apparatus through the gas pipelines;

i) injecting gases into the inner airbags and the outer airbag to inflate the airbags, and sealing openings of the inner airbags and the outer airbag through the sealing structure; adding a cell culture solution into the culture bottle, and delivering the cell culture solution into the artificial atrium fitting body through the fluid delivery apparatus; and j) enabling the inner airbags and the outer airbag to stretch or extrude the artificial atrium fitting body in opposite directions along the same axial direction, controlling the inflation and deflation amplitudes to be 0.1 mm, controlling the rhythm to be 100 times per minute, and controlling inflation and deflation amplitudes and rhythm ranges of the inner airbags and the outer airbag through the airbag controller, so that in the inflation and deflation processes of the inner airbags and the outer airbag, on one hand, the culture solution flows or permeates through a microporous structure of the hydrogel in the organ fitting body, and needs of growth proliferation and metabolism of cells in each area are met; and on the other hand, the artificial atrium fitting body is stressed by a three-dimensional tension-compression stress, connection is established among the cells, and orientated growth and arrangement of the cells may be realized.

Embodiment 3: A Full-Function Artificial Liver Fitting Body as Well as Preparation and Culture Methods Thereof The preparation and culture methods comprise the following steps:

a) designing a shape structure, a branch arterial system structure, a branch venous system structure, a branch nervous system structure and a cortex layer structure of a full-function artificial liver respectively by adopting a three-dimensional computer modeling method;

b) preparing cortex layer molds with different diameters and a three-dimensional skeleton structure of the branch arterial systems, the branch venous systems and the branch nervous systems by adopting the in-mold pouring technology, wherein the cortex layer molds with different diameters are divided into an upper part and a lower part; respectively preparing 1% of sodium alga acid mixture containing hepatic cells, hepatic stem cells, adipose-derived stem cells, Schwann's cells, stellate cells and biliary epithelial cells, wherein a density of the mixed hepatic cells, hepatic stem cells, adipose-derived stem cells, Schwann's cells, stellate cells and biliary epithelial cells is $10^6$ cells per mL; and adding cell cryopreservation agent glycerin with a mass percentage of 6%, an endothelial cell growth factor with a mass percentage of 0.1% and an anticoagulant heparin with a mass percentage of 1%;

c) putting the three-dimensional skeleton structure of at least one group of the branch arterial systems, one group of the branch venous systems and the branch nervous system in the lower half part of the cortex layer mold with a smallest diameter, pouring the sodium alga acid mixture containing the hepatic cells and the hepatic stem cells among the branch arterial systems, the branch venous systems, the branch nervous systems and the lower half part of the cortex layer mold, cross-linking sodium alga acid molecules by using a calcium chloride solution with a mass percentage of 1% to form a lower part of a differentiation area at, and spraying or injecting a fibrinogen mixture containing the adipose-derived stem cells and growth factors on the structure to form the docking area;

d) putting another group of branch arterial systems, the branch venous systems, the branch nervous systems and the upper half part of the cortex layer mold with the smallest diameter on the docking area, and forming the lower part of the differentiation area according to the method in the step c);

e) sequentially sleeving the lower half part and the upper half part of a second cortex layer mold with a larger diameter on an outer part of an upper half part and a lower half part of the prepared differentiation area, pouring the sodium alga acid solution containing the hepatic stem cells and the adipose-derived stem cells into a gap, cross-linking sodium alga acid molecules by using the calcium chloride solution with a mass percentage of 1%, and removing the second cortex layer mold to form a main body three-dimensional skeleton structure containing the differentiation area and the growth area;

f) coating a synthetic polymer polyurethane layer with a mass-volume percentage of 1% outside the main body three-dimensional skeleton structure containing the differentiation area and the growth area, and extracting with an organic solvent to form the full-function artificial liver containing the cortex layer structure;

g) manufacturing inner airbags and an outer airbag, enabling shapes of the inner airbags to be consistent with shapes of an arterial system and a venous system in the full-function artificial liver fitting body, and disinfecting for later use;

h) respectively putting the inner airbags into the branch arterial systems and the branch venous systems, putting the full-function artificial liver fitting body with the inner airbags into the outer airbag together, connecting a branch artery inner airbag and a branch vein inner airbag with the inner airbag gas delivery apparatus through the gas pipelines, and connecting the outer airbag with the outer airbag gas delivery apparatus through the gas pipelines;

i) injecting gases into the inner airbags and the outer airbag to inflate the airbags, and sealing openings of the inner airbags and the outer airbag through the sealing structure; adding a cell culture solution into the culture bottle, and delivering the cell culture solution into the artificial heart fitting body through the fluid delivery apparatus; and j) enabling the inner airbags and the outer airbag to stretch or extrude the artificial liver fitting body in opposite directions along the same axial direction, controlling the inflation and deflation amplitudes to be 0.5 mm, controlling the rhythm to be 80 times per minute, and controlling inflation and deflation amplitudes and rhythm ranges of the inner airbags and the outer airbag through the airbag controller, so that in the inflation and deflation processes of the inner airbags and the outer airbag, on one hand, the culture solution flows or permeates through a microporous structure of the hydrogel in the organ fitting body, and needs of growth proliferation and metabolism of cells in each area are met; and on the other hand, the artificial liver fitting body is stressed by a three-dimensional tension-compression stress, connection is established among the cells, and orientated growth and arrangement of the cells may be realized.

Embodiment 4: A Full-Function Artificial Kidney Fitting Body as Well as Preparation and Culture Methods Thereof The preparation and culture methods comprise the following steps:

a) designing a shape structure, a branch arterial system structure, a branch venous system structure, a branch nervous system structure and a cortex layer structure of a full-function artificial kidney respectively by adopting a three-dimensional computer modeling method;

b) preparing cortex layer molds with different diameters and a three-dimensional skeleton structure of the branch arterial systems, the branch venous systems and the branch nervous systems by adopting the in-mold pouring technology, wherein the cortex layer molds with different diameters are divided into an upper part and a lower part; and respectively preparing 1% of fibrinogen mixture containing cardiac muscle cells, adipose-derived stem cells and Schwann's cells, wherein a density of the mixed cardiac muscle cells is $10^3$ cells per mL, a density of the adipose-derived stem cells is $10^5$ cells per mL, and a density of the Schwann's cells is $10^7$ cells per mL; adding cell cryopreservation agent glycerin with a mass percentage of 5%, an endothelial cell growth factor with a mass percentage of 0.2% and an anticoagulant heparin with a mass percentage of 1%;

c) putting the three-dimensional skeleton structure of at least one group of the branch arterial systems, one group of the branch venous systems and the branch nervous system in the lower half part of the cortex layer mold with the smallest diameter, pouring the fibrinogen mixture containing the cardiac muscle cells and the adipose-derived stem cells among the branch arterial systems, the branch venous systems, the branch nervous systems and the lower half part of the cortex layer mold, polymerizing fibrinogen molecules by using a thrombin with a mass percentage of 1% to form a lower part of the differentiation area, and spraying or injecting the fibrinogen mixture containing the adipose-derived stem cells and endothelial growth factors on the structure to form the docking area;

d) putting another group of branch arterial systems, the branch venous systems, the branch nervous systems and the upper half part of the cortex layer mold with the smallest diameter on the docking area, and forming a lower part of a differentiation area according to the method in the step c);

e) sequentially sleeving the lower half part and the upper half part of a second cortex layer mold with a larger diameter at on an outer part of an upper half part and a lower half part of the prepared differentiation area, pouring the fibrinogen solution containing the adipose-derived stem cells into a gap, polymerizing fibrinogen molecules by using the thrombin with a mass percentage of 1% and removing the second cortex layer mold to form a main body three-dimensional skeleton structure containing the differentiation area and the growth area;

f) coating a synthetic polymer polyurethane layer with a mass-volume percentage of 1% outside the main body three-dimensional skeleton structure containing the differentiation area and the growth area, and extracting with an organic solvent to form the full-function artificial kidney containing the cortex layer structure;

g) manufacturing inner airbags and an outer airbag, enabling shapes of the inner airbags to be consistent with shapes of an arterial system and a venous system in the full-function artificial kidney fitting body, and disinfecting for later use;

h) respectively putting the inner airbags into the branch arterial systems and the branch venous systems, putting the full-function artificial kidney fitting body with the inner airbags into the outer airbag together, connecting a branch artery inner airbag and a branch vein inner airbag with the inner airbag gas delivery apparatus through the gas pipelines, and connecting the outer airbag with the outer airbag gas delivery apparatus through the gas pipelines;

i) injecting gases into the inner airbags and the outer airbag to inflate the airbags, and sealing openings of the inner airbags and the outer airbag through the sealing structure; adding a cell culture solution into the culture bottle, and delivering the cell culture solution into the artificial kidney fitting body through the fluid delivery apparatus; and j) enabling the inner airbags and the outer airbag to stretch or extrude the artificial kidney fitting body in opposite directions along the same axial direction, controlling the inflation and deflation amplitudes to be 0.1 mm, controlling the rhythm to be 100 times per minute, and controlling inflation and deflation amplitudes and rhythm ranges of the inner airbags and the outer airbag through the airbag controller, so that in the inflation and deflation processes of the inner airbags and the outer airbag, on one hand, the culture solution flows or permeates through a microporous structure of the hydrogel in the organ fitting body, and needs of growth proliferation and metabolism of cells in each area are met; and on the other hand, the artificial atrium fitting body is stressed by a three-dimensional tension-compression stress, connection is established among the cells, and orientated growth and arrangement of the cells may be realized.

Embodiment 5: A Full-Function Artificial Pancreas Fitting Body as Well as Preparation and Culture Methods Thereof The preparation and culture methods comprise the following steps:

a) designing a shape structure, a branch arterial system structure, a branch venous system structure, a branch nervous system structure and a cortex layer structure of a full-function artificial pancreas respectively by adopting a three-dimensional computer modeling method;

b) preparing cortex layer molds with different diameters and a three-dimensional skeleton structure of the branch arterial systems, the branch venous systems and the branch nervous systems by adopting the in-mold pouring technology, wherein the cortex layer molds with different diameters are divided into an upper part and a lower part; and respectively preparing 1% of fibrinogen mixture containing islet cells (i.e. beta cells), adipose-derived stem cells and Schwann's cells, wherein a density of the mixed islet cells (i.e. beta cells) is $10^3$ cells per mL, a density of the adipose-derived stem cells is $10^5$ cells per mL, and a density of the Schwann's cells is $10^7$ cells per mL; and adding cell cryopreservation agent glycerin with a mass percentage of 5%, an endothelial cell growth factor with a mass percentage of 0.2% and anticoagulant heparin with a mass percentage of 1%;

c) putting the three-dimensional skeleton structure of at least one group of the branch arterial systems, one group of the branch venous systems and the branch nervous system into the lower half part of the cortex layer mold with the smallest diameter, pouring the fibrinogen mixture containing the islet cells (i.e. beta cells) and the adipose-derived stem cells among the branch arterial systems, the branch venous systems, the branch nervous systems and the lower half part of the cortex layer mold, polymerizing fibrinogen molecules by using a thrombin with a mass percentage of 1% to form a lower part of a differentiation area, and spraying or injecting the fibrinogen mixture containing the adipose-derived stem cells and endothelial growth factors on the structure to form the docking area;

d) putting another group of branch arterial systems, the branch venous systems, the branch nervous systems and the upper half part of the cortex layer mold with the smallest diameter on the docking area, and forming a lower part of the differentiation area at according to the method in the step c);

e) sequentially sleeving the lower half part and the upper half part of a second cortex layer mold with a larger diameter on an outer part of an upper half part and a lower half part of the prepared differentiation area, pouring the fibrinogen solution containing the adipose-derived stem cells into a gap, polymerizing fibrinogen molecules by using the thrombin with the mass percentage of 1%, removing the second cortex layer mold, and forming a main body three-dimensional skeleton structure containing the differentiation area and the growth area;

f) coating a synthetic polymer polyurethane layer with a mass-volume percentage of 1% outside the main body three-dimensional skeleton structure containing the differentiation area and the growth area, and extracting with an organic solvent to form the full-function artificial pancreas containing the cortex layer structure;

g) manufacturing inner airbags and an outer airbag, enabling shapes of the inner airbags to be consistent with shapes of an arterial system and a venous system in the full-function artificial pancreas fitting body, and disinfecting for later use;

h) respectively putting the inner airbags into the branch arterial systems and the branch venous systems, putting the full-function artificial pancreas fitting body with the inner airbags into the outer airbag together, connecting a branch artery inner airbag and a branch vein inner airbag with the inner airbag gas delivery apparatus through the gas pipelines, and connecting the outer airbag with the outer airbag gas delivery apparatus through the gas pipelines;

i) injecting gases into the inner airbags and the outer airbag to inflate the airbags, and sealing openings of the inner airbags and the outer airbag through the sealing structure; adding a cell culture solution into the culture bottle, and delivering the cell culture solution into the artificial pancreas fitting body through the fluid delivery apparatus; and j) enabling the inner airbags and the outer airbag to stretch or extrude the artificial pancreas fitting body in opposite directions along the same axial direction, controlling the inflation and deflation amplitudes to be 0.8 mm, controlling the rhythm to be 70 times per minute, and controlling inflation and deflation amplitudes and rhythm ranges of the inner airbags and the outer airbag through the airbag controller, so that in the inflation and deflation processes of the inner airbags and the outer airbag, on one hand, the culture solution flows or permeates through a microporous structure of the hydrogel in the organ fitting body, and needs of growth proliferation and metabolism of cells in each area are met; and on the other hand, the artificial pancreas fitting body is stressed by a three-dimensional tension-compression stress, connection is established among the cells, and orientated growth and arrangement of the cells may be realized.

Embodiment 6: A Full-Function Artificial Breast Fitting Body as Well as Preparation and Culture Methods Thereof The preparation and culture methods comprise the following steps:

a) designing a shape structure, a branch arterial system structure, a branch venous system structure, a branch nervous system structure and a cortex layer structure of an artificial breast respectively by adopting a three-dimensional computer modeling method;

b) respectively preparing a sodium alga acid solution with a mass percentage of 1% and a carrageenan solution with a mass percentage of 1%; respectively mixing adult adipose cells, adipose-derived stem cells and Schwann's cells with the solution, wherein a density of the mixed adipose cells is $10^6$ cells per mL, a density of the adipose-derived stem cells is $10^3$ cells per mL, and a density of the Schwann's cells is $10^4$ cells per mL; adding cell cryopreservation agent glycerin with a mass percentage of 1%, an endothelial cell growth factor with a mass percentage of 0.2% and an anticoagulant heparin with a mass percentage of 1%; loading the sodium alga acid containing cells and an extracellular matrix solution into an extrusion nozzle assembly of a composite multi-nozzle three-dimensional printing device; and preparing overall cortex layer molds with open upper ends and different diameters and a three-dimensional skeleton structure of the branch arterial systems, the branch venous systems and the branch nervous systems by adopting the 3D printing technology;

c) putting the three-dimensional skeleton structure of at least one group of the branch arterial systems, one group of the branch venous systems and the branch nervous system into the overall cortex layer mold with a smallest diameter, pouring the adipose, the glycerin, the heparin, the carrageenan and the sodium alga acid mixture among the branch arterial systems, the branch venous systems, the branch nervous systems and the overall cortex layer mold, cross-linking sodium alga acid molecules by using a calcium chloride solution with a mass percentage of 1% to form a lower part of a differentiation area, and spraying the sodium alga acid solution containing the adipose-derived stem cells and endothelial cell growth factors on the structure to form the docking area;

d) putting a group of branch venous systems and branch nervous systems on an upper part of the docking area, or putting the branch arterial systems, the branch venous systems and the branch nervous systems, forming an upper part of a differentiation area from an opening at an upper end of the overall cortex layer mold according to a method in the step c), and removing the overall cortex layer mold with the smallest diameter;

e) sleeving a second overall cortex layer mold with a larger diameter on an outer part of the prepared differentiation area, pouring the sodium alga acid solution containing the adipose cells into a gap, cross-linking the sodium alga acid molecules by using the calcium chloride solution with a mass percentage of 1%, and forming a main body three-dimensional skeleton structure containing the differentiation area and the growth area;

f) removing the second overall cortex layer mold, coating a synthetic polymer polycarbonate solution layer with a mass-volume percentage of 5% outside the main body three-dimensional skeleton structure containing the differentiation area and the growth area, and extracting with an organic solvent to form the full-function breast fitting body containing the cortex layer structure;

g) manufacturing inner airbags and an outer airbag, enabling shapes of the inner airbags to be consistent with shapes of an arterial system and a venous system in a full-function artificial breast fitting body, and disinfecting for later use;

h) respectively putting the inner airbags into the branch arterial systems and the branch venous systems, putting the full-function artificial breast fitting body with the inner airbags into the outer airbag together, connecting a branch artery inner airbag and a branch vein inner airbag with the inner airbag gas delivery apparatus through the gas pipelines, and connecting the outer airbag with the outer airbag gas delivery apparatus through the gas pipelines;

i) injecting gases into the inner airbags and the outer airbag to inflate the airbags, and sealing openings of the inner airbags and the outer airbag through the sealing structure; adding a cell culture solution into the culture bottle, and delivering the cell culture solution into the artificial breast fitting body through the fluid delivery apparatus; and j) enabling the inner airbags and the outer airbag to stretch or extrude the artificial breast fitting body along the same direction, controlling the inflation and deflation amplitudes to be 0.6 mm, controlling the rhythm to be 180 times per minute, and controlling inflation and deflation amplitudes and rhythm ranges of the inner airbags and the outer airbag through the airbag controller, so that in the inflation and deflation processes of the inner airbags and the outer airbag, on one hand, the culture solution flows or permeates through a microporous structure of the hydrogel in the organ fitting body, and needs of growth proliferation and metabolism of cells in each area are met; and on the other hand, the artificial breast fitting body is stressed by a three-dimensional tension-compression stress, connection is established among the cells, and orientated growth and arrangement of the cells may be realized.

Embodiment 7: A Full-Function Artificial Lung Fitting Body as Well as Preparation and Culture Methods Thereof The preparation and culture methods comprise the following steps:

a) designing a shape structure, a branch arterial system structure, a branch venous system structure, a branch nervous system structure and a cortex layer structure of an artificial lung respectively by adopting a three-dimensional computer modeling method;

b) respectively preparing a sodium alga acid solution with a mass percentage of 1% and a carrageenan solution with a mass percentage of 1%; respectively mixing adult pulmonary epithelial cells, adipose-derived stem cells and Schwann's cells with the solution, wherein a density of the mixed pulmonary epithelial cells is $10^6$ cells per mL, a density of the adipose-derived stem cells is $10^3$ cells per mL, and a density of the Schwann's cells is $10^4$ cells per mL; adding cell cryopreservation agent glycerin with a mass percentage of 1%, an endothelial cell growth factor with a mass percentage of 0.2% and anticoagulant heparin with a mass percentage of 1%; loading the sodium alga acid containing cells and an extracellular matrix solution into an extrusion nozzle assembly of a composite multi-nozzle three-dimensional printing device; and preparing overall cortex layer molds with open upper ends and different diameters and a three-dimensional skeleton structure of the branch arterial systems, the branch venous systems and the branch nervous systems by adopting the 3D printing technology;

c) putting the three-dimensional skeleton structure of at least one group of the branch arterial systems, one group of the branch venous systems and the branch nervous system in the overall cortex layer mold with a smallest diameter, pouring the pulmonary epithelial cells, the glycerin, the heparin, the carrageenan and the sodium alga acid mixture among the branch arterial systems, the branch venous systems, the branch nervous systems and the overall cortex layer mold, cross-linking sodium alga acid molecules by using a calcium chloride solution with a mass percentage of 1% to form a lower part of a differentiation area, and spraying the sodium alga acid solution containing the adipose-derived stem cells and endothelial cell growth factors on the structure to form the docking area;

d) putting a group of branch venous systems and branch nervous systems on an upper part of the docking area, or putting the branch arterial systems, the branch venous systems and the branch nervous systems, forming an upper part of a differentiation area from an opening at an upper end of the overall cortex layer mold according to a method in the step c), and removing the overall cortex layer mold with the smallest diameter;

e) sleeving a second overall cortex layer mold with a larger diameter on an outer part of the prepared differentiation area, pouring the sodium alga acid solution containing the adipose-derived stem cells into a gap, cross-linking sodium alga acid molecules by using the calcium chloride solution with the mass percentage of 1%, and forming a main body three-dimensional skeleton structure containing the differentiation area and the growth area;

f) removing the second overall cortex layer mold, coating a synthetic polymer polycarbonate solution layer with a mass-volume percentage of 5% outside the main body three-dimensional skeleton structure containing the differentiation area and the growth area, and extracting with an organic solvent to form the full-function lung fitting body containing the cortex layer structure;

g) manufacturing inner airbags and an outer airbag, enabling shapes of the inner airbags to be consistent with shapes of an arterial system and a venous system in a full-function artificial lung fitting body, and disinfecting for later use;

h) respectively putting the inner airbags into the branch arterial systems and the branch venous systems, putting the full-function artificial lung fitting body with the inner airbags into the outer airbag together, connecting a branch artery inner airbag and a branch vein inner airbag with the inner airbag gas delivery apparatus through the gas pipelines, and connecting the outer airbag with the outer airbag gas delivery apparatus through the gas pipelines;

i) injecting gases into the inner airbags and the outer airbag to inflate the airbags, and sealing openings of the inner airbags and the outer airbag through the sealing structure; adding a cell culture solution into the culture bottle, and delivering the cell culture solution into the artificial lung fitting body through the fluid delivery apparatus; and j) enabling the inner airbags and the outer airbag to stretch or extrude the artificial lung fitting body along the same direction, controlling the inflation and deflation amplitudes to be 0.6 mm, controlling the rhythm to be 180 times per minute, and controlling inflation and deflation amplitudes and rhythm ranges of the inner airbags and the outer airbag through the airbag controller, so that in the inflation and deflation processes of the inner airbags and the outer airbag, on one hand, the culture solution flows or permeates through a microporous structure of the hydrogel in the organ fitting body, and needs of growth proliferation and metabolism of cells in each area are met; and on the other hand, the artificial lung fitting body is stressed by a three-dimensional tension-compression stress, connection is established among the cells, and orientated growth and arrangement of the cells may be realized.

Embodiment 8: An Artificial Bone Fitting Body as Well as Preparation and Culture Methods Thereof The preparation and culture methods comprise the following steps:

a) designing a shape structure, a branch arterial system structure, a branch venous system structure, a branch nervous system structure and a cortex layer structure of a large segment of artificial bone respectively by adopting a three-dimensional computer modeling method;

b) respectively preparing a dextrose solution with a mass percentage of 2%, a chitosan solution with a mass percentage of 1% and a fibrinogen solution with a mass percentage of 1%, wherein hydroxyapatite with a mass percentage of 10% is compounded in the solution; respectively mixing adult bone cells, bone marrow stem cells and Schwann's cells with the mixture, wherein a density of the mixed adult bone cells is $10^2$ cells per mL, a density of the bone marrow stem cells is $10^3$ cells per mL, and a density of the Schwann's cells is $10^6$ cells per mL; loading the sodium alga acid containing cells and an extracellular matrix solution into an extrusion nozzle assembly of a composite multi-nozzle three-dimensional printing device; and preparing overall cortex layer molds with open upper ends and different diameters and a three-dimensional skeleton structure of the branch arterial systems, the branch venous systems and the branch nervous systems by adopting the 3D printing technology;

c) putting the three-dimensional skeleton structure of at least one group of the branch arterial systems, one a group of the branch venous systems and the branch nervous system in the overall cortex layer mold with a smallest diameter, pouring the fibrinogen mixture containing the adult bone cells and the hydroxyapatite among the branch arterial systems, the branch venous systems, the branch nervous systems and the overall cortex layer mold, polymerizing fibrinogen molecules by using a thrombin solution with a mass percentage of 1% to form a lower part of a differentiation area, and spraying the fibrinogen solution containing the bone marrow stem cells and the hydroxyapatite on the structure to form the docking area;

d) putting a group of branch venous systems and branch nervous systems on an upper part of the docking area, or putting the branch arterial systems, the branch venous systems and the branch nervous systems, forming an upper part of a differentiation area from an opening at an upper end of the overall cortex layer mold according to a method in the step c), and removing the overall cortex layer mold with the smallest diameter;

e) sleeving a second overall cortex layer mold with a larger diameter on an outer part of the prepared differentiation area, pouring the mixture of the dextrose, chitosan, fibrinogen and hydroxyapatite containing the adipose-derived stem cells into a gap, polymerizing fibrinogen molecules by using the thrombin solution with a mass percentage of 1%, and forming a main body three-dimensional skeleton structure containing the differentiation area and the growth area;

f) removing the second overall cortex layer mold, coating a synthetic polymer polypropylene solution layer with a mass-volume percentage of 10% outside the main body three-dimensional skeleton structure containing the differentiation area and the growth area, and extracting with an organic solvent to form the full-function artificial bone fitting body containing the cortex layer structure;

g) manufacturing inner airbags and an outer airbag, enabling shapes of the inner airbags to be consistent with shapes of an arterial system and a venous system in the full-function artificial bone fitting body, and disinfecting for later use;

h) respectively putting the inner airbags into the branch arterial systems and the branch venous systems, putting the full-function artificial bone fitting body with the inner airbags into the outer airbag together, connecting a branch artery inner airbag and a branch vein inner airbag with the inner airbag gas delivery apparatus through the gas pipelines, and connecting the outer airbag with the outer airbag gas delivery apparatus through the gas pipelines;

i) injecting gases into the inner airbags and the outer airbag to inflate the airbags, and sealing openings of the inner airbags and the outer airbag through the sealing structure; adding a cell culture solution into the culture bottle, and delivering the cell culture solution into the artificial bone fitting body through the fluid delivery apparatus; and j) enabling the inner airbags and the outer airbag to stretch or extrude the artificial bone fitting body along opposite directions, controlling the inflation and deflation amplitudes to be 0.1 mm, controlling the rhythm to be 120 times per minute, and controlling inflation and deflation amplitudes and rhythm ranges of the inner airbags and the outer airbag through the airbag controller, so that in the inflation and deflation processes of the inner airbags and the outer airbag, on one hand, the culture solution flows or permeates through a microporous structure of the hydrogel in the organ fitting body, and needs of growth proliferation and metabolism of cells in each area are met; and on the other hand, the artificial bone fitting body is stressed by a three-dimensional tension-compression stress, connection is established among the cells, and orientated growth and arrangement of the cells may be realized.

Embodiment 9: An Artificial Bladder Fitting Body as Well as Preparation and Culture Methods Thereof The preparation and culture methods comprise the following steps:

a) designing a shape structure, a branch arterial system structure, a branch venous system structure, a branch nervous system structure and a cortex layer structure of an artificial bladder respectively by adopting a three-dimensional computer modeling method;

b) respectively preparing a sodium alga acid solution with a mass percentage of 2%, a bioactive peptide solution with a mass percentage of 1% and an extracellular matrix solution with a mass percentage of 1%; respectively mixing fibroblast, adipose-derived stem cells and Schwann's cells with the solution, wherein a density of the mixed fibroblast is $10^2$ cells per mL, a density of the adipose-derived stem cells is $10^3$ cells per mL, and a density of the Schwann's cells is $10^6$ cells per mL; adding cell cryopreservation agent glycerin with a mass percentage of 3%, an endothelial cell growth factor with a mass percentage of 0.1% and anticoagulant heparin with a mass percentage of 1%; loading the sodium alga acid containing cells and the extracellular matrix solution into an extrusion nozzle assembly of a composite multi-nozzle three-dimensional printing device; and preparing overall cortex layer molds with open upper ends and different diameters and a three-dimensional skeleton structure of the branch arterial systems, the branch venous systems and the branch nervous systems by adopting the 3D printing technology;

c) putting the three-dimensional skeleton structure of at least one group of the branch arterial systems, one group of the branch venous systems and the branch nervous system in the overall cortex layer mold with a smallest diameter, pouring the solution containing the fibroblast, the sodium alga acid, the glycerin, the heparin and the extracellular matrix among the branch arterial systems, the branch venous systems, the branch nervous systems and the overall cortex layer mold, cross-linking sodium alga acid molecules by using a calcium chloride solution with a mass percentage of 1% to form a lower part of a differentiation area, and spraying the sodium alga acid solution containing endothelial cells on the structure to form the docking area;

d) putting a group of branch venous systems and branch nervous systems on an upper part of the docking area, or putting the branch arterial systems, the branch venous systems and the branch nervous systems, forming an upper part of a differentiation area from an opening at an upper end of the overall cortex layer mold according to a method in the step c), and removing the overall cortex layer mold with the smallest diameter;

e) sleeving a second overall cortex layer mold with a larger diameter on an outer part of the prepared differentiation area, pouring the sodium alga acid solution containing the adipose-derived stem cells into a gap, cross-linking sodium alga acid molecules by using the calcium chloride solution with a mass percentage of 1%, and forming a main body three-dimensional skeleton structure containing the differentiation area and the growth area;

f) removing the second overall cortex layer mold, coating a synthetic polymer polyethylene solution layer with a mass-volume percentage of 20% outside the main body three-dimensional skeleton structure containing the differentiation area and the growth area, and extracting with an organic solvent to form the full-function artificial bladder fitting body containing the cortex layer structure;

g) manufacturing inner airbags and an outer airbag, enabling shapes of the inner airbags to be consistent with shapes of an arterial system and a venous system in a full-function artificial bladder fitting body, and disinfecting for later use;

h) respectively putting the inner airbags into the branch arterial systems and the branch venous systems, putting the full-function artificial bladder fitting body with the inner airbags into the outer airbag together, connecting a branch artery inner airbag and a branch vein inner airbag with the inner airbag gas delivery apparatus through the gas pipelines, and connecting the outer airbag with the outer airbag gas delivery apparatus through the gas pipelines;

i) injecting gases into the inner airbags and the outer airbag to inflate the airbags, and sealing openings of the inner airbags and the outer airbag through the sealing structure; adding a cell culture solution into the culture bottle, and delivering the cell culture solution into the artificial bladder fitting body through the fluid delivery apparatus; and j) enabling the inner airbags and the outer airbag to stretch or extrude the artificial bladder fitting body along opposite directions, controlling the inflation and deflation amplitudes to be 1 mm, controlling the rhythm to be 60 times per minute, and controlling inflation and deflation amplitudes and rhythm ranges of the inner airbags and the outer airbag through the airbag controller, so that in the inflation and deflation processes of the inner airbags and the outer airbag, on one hand, the culture solution flows or permeates through a microporous structure of the hydrogel in the organ fitting body, and needs of growth proliferation and metabolism of cells in each area are met; and on the other hand, the artificial bladder fitting body is stressed by a three-dimensional tension-compression stress, connection is established among the cells, and orientated growth and arrangement of the cells may be realized.

Embodiment 10: A Full-Function Artificial Ear Fitting Body as Well as Preparation and Culture Methods Thereof The preparation and culture methods comprise the following steps:

a) designing a shape structure, a branch arterial system structure, a branch venous system structure, a branch nervous system structure and a cortex layer structure of an artificial ear respectively by adopting a three-dimensional computer modeling method;

b) respectively preparing a type I collagen solution with a mass percentage of 1%, a chondroitin sulfate solution with a mass percentage of 0.1% and a hyaluronic acid solution with a mass percentage of 0.2%; respectively mixing bone marrow stem cells, endothelial cells, Schwann's cells and cartilage cells with the solution, wherein a density of the mixed adipose-derived stem cells is $10^5$ cells per mL, a density of the endothelial cells is $10^6$ cells per mL, a density of the Schwann's cells is $10^6$ cells per mL, and a density of the cartilage cells is $10^3$ cells per mL; adding an endothelial cell growth factor with a mass percentage of 0.01% into the type I collagen solution containing the adipose-derived stem cells; loading a polymer solution containing different cells and a mixture into an extrusion nozzle assembly of a composite multi-nozzle three-dimensional printing device; and preparing overall cortex layer molds with open upper ends and different diameters and a three-dimensional skeleton structure of the branch arterial systems, the branch venous systems and the branch nervous systems by adopting the 3D printing technology;

c) putting the three-dimensional skeleton structure of at least one group of the branch arterial systems, one group of the branch venous systems and the branch nervous system in the overall cortex layer mold with a smallest diameter, pouring the type I collagen, the chondroitin sulfate and the hyaluronic acid solution containing the cartilage cells among the branch arterial systems, the branch venous systems, the branch nervous systems and the overall cortex layer mold, polymerizing type I collagen molecules in the solution by using a sodium hydroxide solution with a mass percentage of 1%, forming a lower part of a differentiation area, and spraying the type I collagen solution containing the bone marrow stem cells and endothelial cell growth factors on the structure to form the docking area;

d) putting a group of branch venous systems and branch nervous systems on an upper part of the docking area, or putting the branch arterial systems, the branch venous systems and the branch nervous systems, forming an upper part of a differentiation area from an opening at an upper end of the overall cortex layer mold according to a method in the step c), and removing the overall cortex layer mold with the smallest diameter;

e) sleeving a second overall cortex layer mold with a larger diameter on an outer part of the prepared differentiation area, pouring the type I collagen and chondroitin sulfate solution containing the bone marrow stem cells into a gap, and polymerizing the type I collagen molecules in the solution by using the sodium hydroxide solution with a mass percentage of 1% to form a main body three-dimensional skeleton structure containing the differentiation area and the growth area;

f) removing the second overall cortex layer mold, coating a synthetic polymer polyethylene solution layer with a mass-volume percentage of 10% outside the main body three-dimensional skeleton structure containing the differentiation area and the growth area, and extracting with an organic solvent to form the full-function artificial ear fitting body containing the cortex layer structure;

g) manufacturing inner airbags and an outer airbag, enabling shapes of the inner airbags to be consistent with shapes of an arterial system and a venous system in a full-function artificial ear fitting body, and disinfecting for later use;

h) respectively putting the inner airbags into the branch arterial systems and the branch venous systems, putting the full-function artificial ear fitting body with the inner airbags into the outer airbag together, connecting a branch artery inner airbag and a branch vein inner airbag with the inner airbag gas delivery apparatus through the gas pipelines, and connecting the outer airbag with the outer airbag gas delivery apparatus through the gas pipelines;

i) injecting gases into the inner airbags and the outer airbag to inflate the airbags, and sealing openings of the inner airbags and the outer airbag through the sealing structure; adding a cell culture solution into the culture bottle, and delivering the cell culture solution into the artificial ear fitting body through the fluid delivery apparatus; and j) enabling the inner airbags and the outer airbag to radially drive the artificial ear fitting body to inflate and deflate along the same axis, controlling the inflation and deflation amplitudes to be 0.5 mm, controlling the rhythm to be 200 times per minute, and controlling inflation and deflation amplitudes and rhythm ranges of the inner airbags and the outer airbag through the airbag controller, so that in the inflation and deflation processes of the inner airbags and the outer airbag, on one hand, the culture solution flows or permeates through a microporous structure of the hydrogel in the organ fitting body, and needs of growth proliferation and metabolism of cells in each area are met; and on the other hand, the artificial ear fitting body is stressed by a three-dimensional tension-compression stress, connection is established among the cells, and orientated growth and arrangement of the cells may be realized.

Embodiment 11: An Artificial Spleen Fitting Body as Well as Preparation and Culture Methods Thereof The preparation and culture methods comprise the following steps:

a) designing a shape structure, a branch arterial system structure, a branch venous system structure, a branch nervous system structure and a cortex layer structure of an artificial spleen respectively by adopting a three-dimensional computer modeling method;

b) respectively preparing a fibrinogen solution with a mass percentage of 3%; respectively mixing adipose-derived stem cells, endothelial cells, Schwann's cells and spleen cells with the solution, wherein a density of the mixed umbilical cord blood stem cells is $10^5$ cells per mL, a density of the endothelial cells is $10^6$ cells per mL, a density of the Schwann's cells is $10^6$ cells per mL, and a density of the spleen cells is $10^3$ cells per mL; adding an endothelial cell growth factor with a mass percentage of 0.01% into the fibrinogen solution containing the umbilical cord blood stem cells; loading a polymer solution containing different cells and a mixture into an extrusion nozzle assembly of a composite multi-nozzle three-dimensional printing device; and preparing overall cortex layer molds with open upper ends and different diameters and a three-dimensional skeleton structure of the branch arterial systems, the branch venous systems and the branch nervous systems by adopting the 3D printing technology;

c) putting the three-dimensional skeleton structure of at least one group of the branch arterial systems, one group of the branch venous systems and the branch nervous system in the overall cortex layer mold with a smallest diameter, pouring the fibrinogen solution containing the adipose-derived stem cells and endothelial cell growth factors among the branch arterial systems, the branch venous systems, the branch nervous systems and the overall cortex layer mold, polymerizing fibrinogen molecules by using a thrombin solution with a mass percentage of 10%, forming a lower part of a differentiation area, and spraying the fibrinogen solution containing the umbilical cord blood stem cells and the endothelial cell growth factors on the structure to form the docking area;

d) putting a group of branch venous systems and branch nervous systems on an upper part of the docking area, or putting the branch arterial systems, the branch venous systems and the branch nervous systems, forming an upper part of a differentiation area from an opening at an upper end of the overall cortex layer mold according to a method in the step c), and removing the overall cortex layer mold with the smallest diameter;

e) sleeving a second overall cortex layer mold with a larger diameter on an outer part of the prepared differentiation area, pouring the fibrinogen solution containing the umbilical cord blood stem cells into a gap, and polymerizing the fibrinogen molecules by using the thrombin solution with a mass percentage of 10% to form a main body three-dimensional skeleton structure containing the differentiation area and the growth area;

f) removing the second overall cortex layer mold, coating a synthetic polymer polycaprolactone solution layer with a mass-volume percentage of 1% outside the main body three-dimensional skeleton structure containing the differentiation area and the growth area, and extracting with an organic solvent to form the full-function artificial spleen fitting body containing the cortex layer structure;

g) manufacturing inner airbags and an outer airbag, enabling shapes of the inner airbags to be consistent with shapes of an arterial system and a venous system in a full-function artificial spleen fitting body, and disinfecting for later use;

h) respectively putting the inner airbags into the branch arterial systems and the branch venous systems, putting the full-function artificial spleen fitting body with the inner airbags into the outer airbag together, connecting a branch artery inner airbag and a branch vein inner airbag with the inner airbag gas delivery apparatus through the gas pipelines, and connecting the outer airbag with the outer airbag gas delivery apparatus through the gas pipelines;

i) injecting gases into the inner airbags and the outer airbag to inflate the airbags, and sealing openings of the inner airbags and the outer airbag through the sealing structure; adding a cell culture solution into the culture bottle, and delivering the cell culture solution into the artificial spleen fitting body through the fluid delivery apparatus; and j) enabling the inner airbags and the outer airbag to radially drive the spleen fitting body to inflate and deflate along the same axis, controlling the inflation and deflation amplitudes to be 0.5 mm, controlling the rhythm to be 200 times per minute, and controlling inflation and deflation amplitudes and rhythm ranges of the inner airbags and the outer airbag through the airbag controller, so that in the inflation and deflation processes of the inner airbags and the outer airbag, on one hand, the culture solution flows or permeates through a microporous structure of the hydrogel in the organ fitting body, and needs of growth proliferation and metabolism of cells in each area are met; and on the other hand, the spleen fitting body is stressed by a three-dimensional tension-compression stress, connection is established among the cells, and orientated growth and arrangement of the cells may be realized.

Embodiment 12: An Artificial Brain Fitting Body as Well as Preparation and Culture Methods Thereof The preparation and culture methods comprise the following steps:

a) designing a shape structure, a branch arterial system structure, a branch venous system structure, a branch nervous system structure and a cortex layer structure of an artificial brain respectively by adopting a three-dimensional computer modeling method;

b) respectively preparing a fibrinogen solution with a mass percentage of 2%; respectively mixing endothelial cells, bone marrow stem cells, Schwann's cells and neuroglial cells with the solution, wherein a density of the mixed endothelial cells is $10^5$ cells per mL, a density of the bone marrow stem cells is $10^5$ cells per mL, and a density of the neuroglial cells and the Schwann's cells is $10^6$ cells per mL; adding 0.01% of an endothelial cell growth factor and 10% of calcium phosphate into the fibrinogen solution containing the bone marrow stem cells; loading a polymer solution containing different cells and a mixture into an extrusion nozzle assembly of a composite multi-nozzle three-dimensional printing device; and preparing overall cortex layer molds with open upper ends and different diameters and a three-dimensional skeleton structure of the branch arterial systems, the branch venous systems and the branch nervous systems by adopting the 3D printing technology;

c) putting the three-dimensional skeleton structure of at least one group of the branch arterial systems, one group of the branch venous systems and the branch nervous system in the overall cortex layer mold with a smallest diameter, pouring the fibrinogen solution containing the bone marrow stem cells, the endothelial cell growth factor and the calcium phosphate among the branch arterial systems, the branch venous systems, the branch nervous systems and the overall cortex layer mold, polymerizing fibrinogen molecules by using a thrombin solution with a mass percentage of 10%, forming a lower part of a differentiation area, and spraying the fibrinogen solution containing the bone marrow stem cells, the endothelial cell growth factor and the calcium phosphate on the structure to form the docking area;

d) putting a group of branch venous systems and branch nervous systems on an upper part of the docking area, or putting the branch arterial systems, the branch venous systems and the branch nervous systems, forming an upper part of a differentiation area from an opening at an upper end of the overall cortex layer mold according to a method in the step c), and removing the overall cortex layer mold with the smallest diameter;

e) sleeving a second overall cortex layer mold with a larger diameter on an outer part of the prepared differentiation area, pouring the fibrinogen solution containing the bone marrow stem cells and the calcium phosphate into a gap, and polymerizing the fibrinogen molecules by using the thrombin solution with a mass percentage of 10% to form a main body three-dimensional skeleton structure containing the differentiation area and the growth area;

f) removing the second overall cortex layer mold, coating a synthetic polymer polylactide-co-glycolide solution layer with a mass-volume percentage of 30% outside the main body three-dimensional skeleton structure containing the differentiation area and the growth area, and extracting with an organic solvent to form the full-function artificial brain fitting body containing the cortex layer structure;

g) manufacturing inner airbags and an outer airbag, enabling shapes of the inner airbags to be consistent with shapes of an arterial system and a venous system in a full-function artificial brain fitting body, and disinfecting for later use;

h) respectively putting the inner airbags into the branch arterial systems and the branch venous systems, putting the full-function artificial brain fitting body with the inner airbags into the outer airbag together, connecting a branch artery inner airbag and a branch vein inner airbag with the inner airbag gas delivery apparatus through the gas pipelines, and connecting the outer airbag with the outer airbag gas delivery apparatus through the gas pipelines;

i) injecting gases into the inner airbags and the outer airbag to inflate the airbags, and sealing openings of the inner airbags and the outer airbag through the sealing structure; adding a cell culture solution into the culture bottle, and delivering the cell culture solution into the artificial brain fitting body through the fluid delivery apparatus; and j) enabling the inner airbags and the outer airbag to radially drive the brain fitting body to inflate and deflate along the same axis, controlling the inflation and deflation amplitudes to be 1 mm, controlling the rhythm to be 80 times per minute, and controlling inflation and deflation amplitudes and rhythm ranges of the inner airbags and the outer airbag through the airbag controller, so that in the inflation and deflation processes of the inner airbags and the outer airbag, on one hand, the culture solution flows or permeates through a microporous structure of the hydrogel in the organ fitting body, and needs of growth proliferation and metabolism of cells in each area are met; and on the other hand, the brain fitting body is stressed by a three-dimensional tension-compression stress, connection is established among the cells, and orientated growth and arrangement of the cells may be realized.

Embodiment 13: A Uterus Fitting Body as Well as Preparation and Culture Methods Thereof The preparation and culture methods comprise the following steps:

a) designing a shape structure, a branch arterial system structure, a branch venous system structure, a branch nervous system structure and a cortex layer structure of an artificial uterus respectively by adopting a three-dimensional computer modeling method;

b) respectively preparing a sodium alga acid solution with a mass-volume concentration of 1%; respectively mixing fibroblasts, adipose-derived stem cells and Schwann's cells with the solution, wherein a density of the mixed fibroblasts is $10^2$ cells per mL, a density of the adipose-derived stem cells is $10^3$ cells per mL, and a density of the Schwann's cells is $10^6$ cells per mL; loading a polymer solution containing cells into an extrusion nozzle assembly of a composite multi-nozzle three-dimensional printing device; and preparing overall cortex layer molds with open upper ends and different diameters and a three-dimensional skeleton structure of the branch arterial systems, the branch venous systems and the branch nervous systems by adopting the 3D printing technology;

c) putting the three-dimensional skeleton structure of at least one group of the branch arterial systems, one group of the branch venous systems and the branch nervous system in the overall cortex layer mold with a smallest diameter, pouring the sodium alga acid solution containing the fibroblasts among the branch arterial systems, the branch venous systems, the branch nervous systems and the overall cortex layer mold, cross-linking sodium alga acid molecules by using a calcium chloride solution with a mass percentage of 1% to form a lower part of a differentiation area, and spraying the sodium alga acid solution containing the endothelial cells on the structure to form the docking area;

d) putting a group of branch venous systems and branch nervous systems on an upper part of the docking area, or putting the branch arterial systems, the branch venous systems and the branch nervous systems, forming an upper part of a differentiation area from an opening at an upper end of the overall cortex layer mold according to a method in the step c), and removing the overall cortex layer mold with the smallest diameter;

e) sleeving a second overall cortex layer mold with a larger diameter on an outer part of the prepared differentiation area, pouring the sodium alga acid solution containing the adipose-derived stem cells into a gap, cross-linking the sodium alga acid molecules by using the calcium chloride solution with a mass percentage of 1%, and forming a main body three-dimensional skeleton structure containing the differentiation area and the growth area;

f) removing the second overall cortex layer mold, coating a synthetic polymer polyurethane solution layer with a mass-volume percentage of 1% outside the main body three-dimensional skeleton structure containing the differentiation area and the growth area, and extracting with an organic solvent to form the full-function artificial uterus fitting body containing the cortex layer structure;

g) manufacturing inner airbags and an outer airbag, enabling shapes of the inner airbags to be consistent with shapes of an arterial system and a venous system in a full-function artificial uterus fitting body, and disinfecting for later use;

h) respectively putting the inner airbags into the branch arterial systems and the branch venous systems, putting the full-function artificial uterus fitting body with the inner airbags into the outer airbag together, connecting a branch artery inner airbag and a branch vein inner airbag with the inner airbag gas delivery apparatus through the gas pipelines, and connecting the outer airbag with the outer airbag gas delivery apparatus through the gas pipelines;

i) injecting gases into the inner airbags and the outer airbag to inflate the airbags, and sealing openings of the inner airbags and the outer airbag through the sealing structure; adding a cell culture solution into the culture bottle, and delivering the cell culture solution into the artificial uterus fitting body through the fluid delivery apparatus; and j) enabling the inner airbags and the outer airbag to stretch or extrude the artificial uterus fitting body along opposite directions, controlling the inflation and deflation amplitudes to be 1 mm, controlling the rhythm to be 60 times per minute, and controlling inflation and deflation amplitudes and rhythm ranges of the inner airbags and the outer airbag through the airbag controller, so that in the inflation and deflation processes of the inner airbags and the outer airbag, on one hand, the culture solution flows or permeates through a microporous structure of the hydrogel in the organ fitting body, and needs of growth proliferation and metabolism of cells in each area are met; and on the other hand, the uterus fitting body is stressed by a three-dimensional tension-compression stress, connection is established among the cells, and orientated growth and arrangement of the cells may be realized.

Embodiment 14: An Artificial Skin Fitting Body as Well as Preparation and Culture Methods Thereof The preparation and culture methods comprise the following steps:

a) designing a shape structure, a branch arterial system structure, a branch venous system structure, a branch nervous system structure and a cortex layer structure of artificial skin respectively by adopting a three-dimensional computer modeling method;

b) respectively preparing a chitosan solution with a mass-volume concentration of 0.1% and a gelatin solution with a mass-volume concentration of 20%, and mixing the two solutions according to a volume ratio of 1:1; respectively mixing fibroblasts, adipose-derived stem cells and Schwann's cells with the solution, wherein a density of the mixed fibroblasts is $10^7$ cells per mL, a density of the adipose-derived stem cells is $10^4$ cells per mL, and a density of the Schwann's cells is $10^6$ cells per mL; loading a polymer solution containing cells into an extrusion nozzle assembly of a composite multi-nozzle three-dimensional printing device; and preparing overall cortex layer molds with open upper ends and different diameters and a three-dimensional skeleton structure of the branch arterial systems, the branch venous systems and the branch nervous systems by adopting the 3D printing technology;

c) putting the three-dimensional skeleton structure of at least one group of the branch arterial systems, one group of the branch venous systems and the branch nervous system in the overall cortex layer mold with a smallest diameter, pouring the chitosan and gelatin mixed solution containing the fibroblasts among the branch arterial systems, the branch venous systems, the branch nervous systems and the overall cortex layer mold, cross-linking the chitosan by using a calcium polyphosphate solution with a mass percentage of 1% to form a lower part of a differentiation area, and spraying the chitosan and gelatin mixed solution containing the endothelial cells on the structure to form the docking area;

d) putting a group of branch venous systems and branch nervous systems on an upper part of the docking area, or putting the branch arterial systems, the branch venous systems and the branch nervous systems, forming an upper part of a differentiation area from an opening at an upper end of the overall cortex layer mold according to a method in the step c), and removing the overall cortex layer mold with the smallest diameter;

e) sleeving a second overall cortex layer mold with a larger diameter on an outer part of the prepared differentiation area, pouring the chitosan and gelatin mixed solution containing the adipose-derived stem cells into a gap, cross-linking chitosan molecules by using the calcium polyphosphate solution with the mass percentage of 1%, and forming a main body three-dimensional skeleton structure containing the differentiation area and the growth area;

f) removing the second overall cortex layer mold, coating a synthetic polymer polyurethane solution layer with a mass-volume percentage of 0.1% outside the main body three-dimensional skeleton structure containing the differentiation area and the growth area, and extracting with an organic solvent to form the full-function skin fitting body containing the cortex layer structure;

g) manufacturing inner airbags and an outer airbag, enabling shapes of the inner airbags to be consistent with shapes of an arterial system and a venous system in a full-function skin fitting body, and disinfecting for later use;

h) respectively putting the inner airbags into the branch arterial systems and the branch venous systems, putting the full-function skin fitting body with the inner airbags into the outer airbag together, connecting a branch artery inner airbag and a branch vein inner airbag with the inner airbag gas delivery apparatus through the gas pipelines, and connecting the outer airbag with the outer airbag gas delivery apparatus through the gas pipelines;

i) injecting gases into the inner airbags and the outer airbag to inflate the airbags, and sealing openings of the inner airbags and the outer airbag through the sealing structure; adding a cell culture solution into the culture bottle, and delivering the cell culture solution into the skin fitting body through the fluid delivery apparatus; and j) enabling the inner airbags and the outer airbag to radially drive the skin fitting body to inflate and deflate along the same axis, controlling the inflation and deflation amplitudes to be 0.01 mm, controlling the rhythm to be 20 times per minute, and controlling inflation and deflation amplitudes and rhythm ranges of the inner airbags and the outer airbag through the airbag controller, so that in the inflation and deflation processes of the inner airbags and the outer airbag, on one hand, the culture solution flows or permeates through a microporous structure of the hydrogel in the organ fitting body, and needs of growth proliferation and metabolism of cells in each area are met; and on the other hand, the skin fitting body is stressed by a three-dimensional tension-compression stress, connection is established among the cells, and orientated growth and arrangement of the cells may be realized.

What is claimed is:

1. A full-function artificial organ fitting body, comprising a cortex layer (101) and an organ body tissue area (102), wherein the organ body tissue area comprises a growth area (103), a differentiation area (104), a docking area (105), a branch arterial system (106), a branch nervous system (107) and a branch venous system (108); a structural shape of the cortex layer (101) simulates an appearance of each organ of an animal; the branch arterial system (106), the branch nervous system (107) and the branch venous system (108) are distributed in the differentiation area (104) and form a main body three-dimensional skeleton structure with the outer growth area (103) and the middle docking area (105); the branch arterial system (106) comprises a main artery and arterial branches; the branch venous system (108) comprises a main vein and venous branches; the arterial branches and the venous branches are respectively connected with the middle docking area (105); the branch nervous system (108) comprises a main nerve tract and nerve tract branches; the differentiation area (104) is composed of natural polymeric hydrogel containing adult cells, or natural polymeric hydrogel containing growth factors and stem cells; the growth area (103) is composed of natural polymeric hydrogel containing stem cells; the docking area (105) is composed of natural polymeric hydrogel containing endothelial cells, or natural polymeric hydrogel containing the growth factors and the stem cells; the branch nervous system (108) penetrates through the docking area (105) and is continuously penetrated; the branch arterial system (106) comprises at least one fluid inlet, at least contains one fluid outlet or does not have any outlet; the branch venous system (108) comprises at least one fluid inlet and at least one fluid outlet; the cortex layer (101) is a synthetic polymeric material and is divided into an upper part and a lower part; and the branch arterial system (106), the branch nervous system (107) and the branch venous system (108) are composed of the cell-containing natural polymeric hydrogel through layered perfusion by using a 3D printing layer-by-layer stacking or in-mold pouring technology;

wherein the adult cells are at least one of cardiac muscle cells, hepatic cells, islet cells, stellate cells, osteoblast, cartilage cells, smooth muscle cells, fibroblast, endothelial cells, nephrocyte, Schwann's cells, neuroglial cells, epithelial cells, adipose cells, spleen cells, uterus cells and adipose cells; and the stem cells are at least one of mesenchymal stem cells, umbilical cord blood stem cells, bone marrow stem cells, embryonic stem cells and induced pluripotent stem cells;

wherein the branch arterial system and the branch venous system comprise at least one endovascular cortex layer composed of endothelial cells; the branch nervous system comprises a fiber bundle containing at least one kind of nerve cells; inner diameters of the arterial branches and the venous branches are 0.01-5 mm, and diameters of the nerve tract branches are 0.01-5 mm; and a layer thickness of the cell-containing hydrogel in the growth area, the differentiation area and the docking area is 0.01-20 mm wherein the natural polymeric hydrogel in the differentiation area, the growth area and the docking area of the artificial organ is at least one of sodium alga acid with a mass percentage of 0.1-20%, collagen, dextrose, fibrinogen, bioactive peptide, gelatin, chitosan, an extracellular matrix, gelose, laminin, chondroitin sulfate, carrageenan, protein polysaccharide and a hyaluronic acid solution; one or more of inorganic salt with a mass percentage of 0.01-10%, an anticoagulation factor and a cryopreservation factor are compounded in the natural polymeric hydrogel; the cortex layer is at least one of synthetic polymeric polyurethane, polyethylene, polypropylene, polyvinyl chloride, polycaprolactone, polycarbonate, polyethylene glycol, poly(lactic-co-glycolic acid), polyester and polyglycolic acid ester; and a solvent of the synthetic polymeric solution is tetraethylene glycol or 1,4-dioxane, and a mass-volume percentage of the synthetic polymeric solution is 0.1-30%.

* * * * *